(12) United States Patent
Cesa et al.

(10) Patent No.: US 8,623,289 B2
(45) Date of Patent: Jan. 7, 2014

(54) SINGLE USE STERILIZATION CONTAINER

(75) Inventors: Joseph A. Cesa, Cumming, GA (US); Laureen C. Clark, Johns Creek, GA (US); John K. Clay, Milford, CT (US); Steven Scott Friderich, Roswell, GA (US); Sean P. Gorman, Cumming, GA (US); David Hernandez, Mableton, GA (US); Denise E. O'Connor, Elizabeth Bay (AU); Corinna Schwarz, Roswell, GA (US); Tara Denise Smith, Marietta, GA (US); James Troy Starkey, North Haven, CT (US); Daniel P. Sterling, Norwalk, CT (US)

(73) Assignee: Kimberly-Clark Worldwide Inc., Neenah, WI (US)

( * ) Notice: Subject to any disclaimer, the term of this patent is extended or adjusted under 35 U.S.C. 154(b) by 880 days.

(21) Appl. No.: 12/639,350

(22) Filed: Dec. 16, 2009

(65) Prior Publication Data

US 2010/0154353 A1  Jun. 24, 2010

Related U.S. Application Data

(63) Continuation-in-part of application No. 12/317,657, filed on Dec. 24, 2008, now Pat. No. 7,942,264.

(51) Int. Cl.
| | |
|---|---|
| *A61L 2/00* | (2006.01) |
| *B65D 83/10* | (2006.01) |
| *B65D 17/32* | (2006.01) |
| *B65D 17/34* | (2006.01) |
| *A61B 17/06* | (2006.01) |
| *E05B 39/02* | (2006.01) |

(52) U.S. Cl.
USPC ........... 422/300; 422/297; 206/439; 206/370; 206/363; 220/371; 220/266; 220/324; 292/243; 292/307 R

(58) Field of Classification Search
USPC .............. 422/26, 28, 297, 300, 939; 206/439, 206/370, 363, 484.1; 220/371, 268, 324; 55/279, 511; 292/243, 307 R
See application file for complete search history.

(56) References Cited

U.S. PATENT DOCUMENTS

| | | |
|---|---|---|
| 2,990,948 A | 7/1961 | Zackheim |
| 3,338,992 A | 8/1967 | Kinney |

(Continued)

FOREIGN PATENT DOCUMENTS

| | | |
|---|---|---|
| EP | 0 307 173 A1 | 3/1989 |
| EP | 1 762 503 A1 | 3/2007 |
| JP | 2001-286538 A | 10/2001 |
| WO | WO 2007/066359 A1 | 6/2007 |

OTHER PUBLICATIONS

American Society for Testing Materials (ASTM) Designation: E 96-80, "Standard Test Methods for Water Vapor Transmission of Materials," pp. 742-751, published Feb. 1981.

(Continued)

*Primary Examiner* — Monzer Chorbaji
(74) *Attorney, Agent, or Firm* — Karl V. Sidor

(57) ABSTRACT

A non-reusable, locking container for sterilizing and storing surgical materials and presenting surgical materials in a sterilized condition. The non-reusable, locking sterilization container includes a tray, a lid, a permeable filter, a non-reusable lock and a frangible release that limit the container to only a single sterilization cycle or single use.

15 Claims, 17 Drawing Sheets

(56) References Cited

U.S. PATENT DOCUMENTS

| | | |
|---|---|---|
| 3,341,394 A | 9/1967 | Kinney |
| 3,478,868 A | 11/1969 | Nerenberg et al. |
| 3,502,538 A | 3/1970 | Petersen |
| 3,502,763 A | 3/1970 | Hartmann |
| 3,542,615 A | 11/1970 | Dobo et al. |
| 3,692,618 A | 9/1972 | Dorschner et al. |
| 3,770,119 A | 11/1973 | Hultberg et al. |
| 3,802,817 A | 4/1974 | Matsuki et al. |
| 3,849,241 A | 11/1974 | Butin et al. |
| 3,946,871 A | 3/1976 | Sturm |
| 3,946,872 A | 3/1976 | Sturm |
| 3,954,174 A | 5/1976 | Kraus |
| 4,022,324 A | 5/1977 | Schuster |
| 4,041,203 A | 8/1977 | Brock et al. |
| 4,042,109 A | 8/1977 | Barcan |
| 4,049,121 A | 9/1977 | White |
| 4,124,141 A | 11/1978 | Armentrout et al. |
| 4,340,563 A | 7/1982 | Appel et al. |
| 4,417,658 A | 11/1983 | Gardner et al. |
| 4,466,552 A | 8/1984 | Butterworth et al. |
| 4,509,196 A | 4/1985 | Sak et al. |
| 4,553,669 A | 11/1985 | Butterworth et al. |
| 4,644,586 A | 2/1987 | Padgett |
| 4,660,721 A | 4/1987 | Mykleby |
| 4,661,326 A | 4/1987 | Schainholz |
| 4,671,943 A | 6/1987 | Wahlquist |
| 4,706,839 A | 11/1987 | Spence |
| 4,728,504 A | 3/1988 | Nichols |
| 4,766,029 A | 8/1988 | Brock et al. |
| 4,783,321 A | 11/1988 | Spence |
| 4,858,821 A | 8/1989 | Bickelhaupt |
| 4,884,694 A | 12/1989 | Sengewald |
| 4,903,837 A | 2/1990 | Duello |
| 4,915,913 A * | 4/1990 | Williams et al. ............... 422/119 |
| 4,919,888 A | 4/1990 | Spence |
| 4,927,073 A | 5/1990 | Esposito |
| 5,069,355 A | 12/1991 | Matuszak |
| 5,169,706 A | 12/1992 | Collier, IV et al. |
| 5,342,673 A | 8/1994 | Bowman et al. |
| 5,382,400 A | 1/1995 | Pike et al. |
| 5,392,917 A | 2/1995 | Alpern et al. |
| 5,464,688 A | 11/1995 | Timmons et al. |
| 5,520,975 A | 5/1996 | Inoue et al. |
| 5,688,394 A | 11/1997 | McBride, Jr. et al. |
| 5,736,043 A | 4/1998 | Nichols et al. |
| 5,823,340 A | 10/1998 | Maihofer |
| 5,830,547 A | 11/1998 | MacKenzie et al. |
| 6,080,456 A | 6/2000 | Fonteyne |
| 6,087,548 A * | 7/2000 | Levy et al. ............... 588/255 |
| 6,162,395 A | 12/2000 | Kowanko |
| 6,217,835 B1 | 4/2001 | Riley et al. |
| 6,312,645 B1 | 11/2001 | Lin et al. |
| 6,312,646 B2 | 11/2001 | Kowanko |
| 6,319,481 B1 | 11/2001 | Banks |
| 6,379,616 B1 | 4/2002 | Sheiman |
| 6,439,625 B1 | 8/2002 | Schainholz et al. |
| 6,468,482 B1 | 10/2002 | Frieze et al. |
| 6,561,352 B2 | 5/2003 | Sherman et al. |
| 6,629,602 B1 | 10/2003 | Heyman |
| 6,889,839 B1 | 5/2005 | Rosten et al. |
| 7,066,329 B2 | 6/2006 | Riley |
| 7,100,768 B2 | 9/2006 | Grimard et al. |
| 7,300,637 B2 | 11/2007 | Lin et al. |
| 7,350,688 B2 | 4/2008 | Sierra-Gomez et al. |
| 2002/0098139 A1 | 7/2002 | Sparks |
| 2003/0118491 A1 | 6/2003 | Frieze et al. |
| 2003/0143136 A1 | 7/2003 | Regan |
| 2003/0183547 A1 | 10/2003 | Heyman |
| 2004/0256269 A1 | 12/2004 | Gleichauf et al. |
| 2005/0145627 A1 | 7/2005 | Stull et al. |
| 2005/0194387 A1 | 9/2005 | Banks |
| 2005/0238530 A1 | 10/2005 | Frieze et al. |
| 2005/0268573 A1 | 12/2005 | Yan |
| 2006/0179793 A1 | 8/2006 | Yewdall et al. |
| 2007/0092398 A1 | 4/2007 | McDonald |
| 2007/0095699 A1 | 5/2007 | Frieze et al. |
| 2008/0000899 A1 | 1/2008 | Baker et al. |
| 2010/0158751 A1 | 6/2010 | Friderich et al. |
| 2010/0158752 A1 | 6/2010 | Friderich et al. |
| 2010/0158753 A1 | 6/2010 | Friderich et al. |
| 2010/0270197 A1 | 10/2010 | Porret et al. |

OTHER PUBLICATIONS

Machine translation of JP Application 2000-108596, which corresponds to JP 2001-286538 A.

* cited by examiner

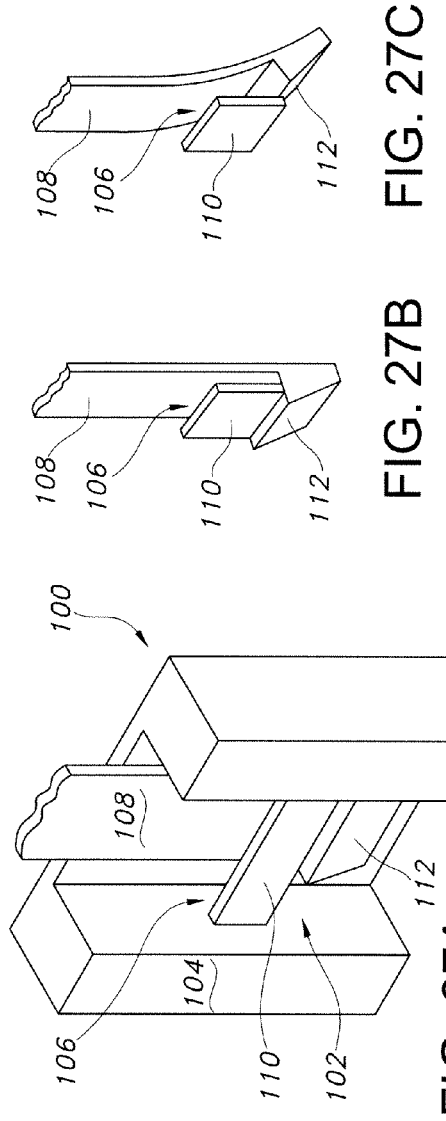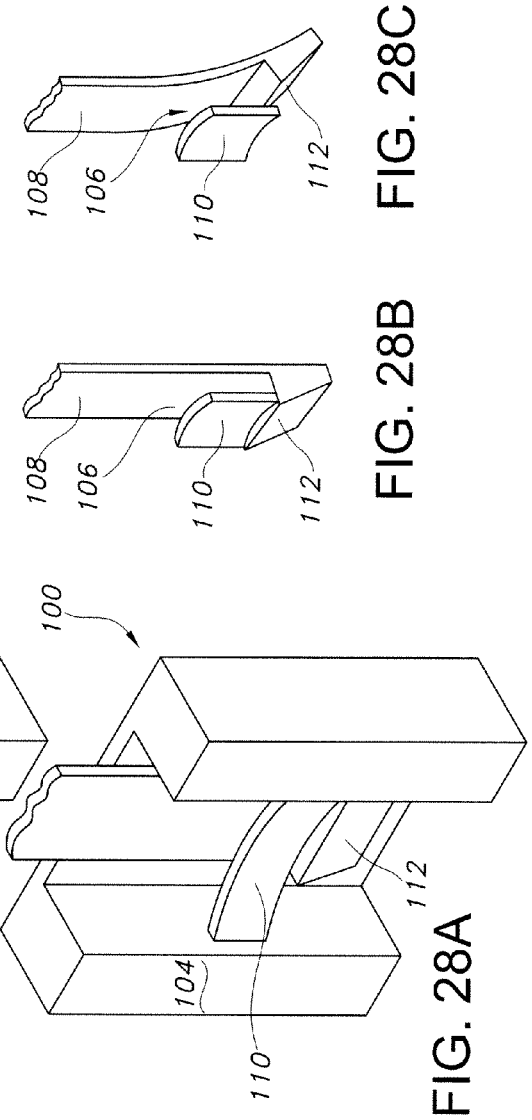

SINGLE USE STERILIZATION CONTAINER

This application is a continuation-in-part of, and claims priority to, U.S. Ser. No. 12/317,657 filed Dec. 24, 2008 now U.S. Pat. No. 7,942,264 entitled "Sterilization Container With Peel Top" by Steven Scott Friderich et al., which is hereby incorporated by reference for all purposes.

BACKGROUND

Sterilization of items used in medical procedures is vital to minimizing the spread of harmful and infectious microbes to patients. Typically, the items used in medical procedures are wrapped with a sterilization wrap made of a gas permeable material or placed in a reusable vented rigid sterilization container. These sterilization wraps or sterilization containers preserve sterility of the items contained therein, as well as the interior portion of these wraps or containers, after the wraps or containers and their respective contents have been channeled through a sterilization process. During a typical sterilization process, the sterilization wraps or vented rigid sterilization containers are placed into a sterilization chamber, and the gas permeable material in the sterilization wrap or vents within the rigid sterilization container allow a gas sterilant to contact the item(s) to be sterilized in the sterilization container.

Examples of current gas sterilization procedures include, gas plasma sterilization, steam sterilization, ethylene oxide sterilization, hydrogen peroxide sterilization, and ozone sterilization. Other sterilization procedures, such as irradiation have also been used.

Although utilization of sterilization wrap and/or use of vented rigid reusable sterilization containers are generally effective, there are certain disadvantages associated with each of these items.

Sterilization wraps are made of a relatively thin, inexpensive, flexible material and have generally low initial cost. However, items to be sterilized are often placed within a metal sterilization tray prior to wrapping the items with sterilization wrap. These sterilization trays have pointed edges or other features that may concentrate forces and generate very small tears or snags if the wrap contacts these features. When wrapped trays are transported on carts or stacked prior to sterilization or after sterilization, other sources of very small tears or breaches in the barrier may develop in the wrap due to pressure or impact. These tears may allow bacteria or other harmful substances to contaminate the items which results in added expense because the items to be sterilized will need to re-handled and re-sterilized at an additional cost.

An additional issue with the use of sterilization wraps is a lack of visibility. Because sterilization wraps generally are not made of transparent material, the medical professional utilizing it cannot visually inspect the items contained therein for content or for assurance that the sterilization procedure has been completed. This can lead to a medical professional opening the wrong sterilization tray during a procedure and/or lead to lack of confidence that the tray is truly sterilized. As a result, trays and articles may require unnecessary re-handling and re-sterilization which wastes both economic and time resources.

With regard to reusable vented rigid sterilization containers, although generally effective, these containers must be thoroughly maintained and cleaned between uses so that they may be re-used. In contrast, sterilization wrap is typically discarded after a single use. Reusable sterilization containers require significant amounts of hospital economic and time resources because staffing levels often need to be increased in order to process and maintain these rigid containers for re-use. Additionally, the longer the containers are in use, the less confidence clinicians have in the sterilization efficacy of the containers. Ultimately, these containers must be repaired, reconditioned, or discarded.

Thus, there remains a need in the art for sterilization containers that are economical provide ease of visual inspection, and that impart confidence in sterility among clinicians.

SUMMARY

The present invention provides a non-reusable, locking container for sterilizing and storing surgical materials and aseptically opening and aseptically presenting surgical materials in a sterilized condition. The non-reusable, locking sterilization container includes a combination of elements that limit the container to only a single sterilization cycle or single use. Generally speaking, the non-reusable, locking sterilization container includes a tray, a lid, a permeable filter, a non-reusable lock and a frangible release.

The tray includes a base, a plurality of sides each having a proximal portion in communication with the base and a distal portion away from the base, and a rim defined by the distal portions of the sides. The rim forms or includes a lower portion of a barrier.

The lid includes a central portion and a lip, the lip forms or includes an upper portion of a barrier. When the lid and the tray are secured together, they define a chamber for containing surgical materials. When the lip and the rim are properly secured together, they form a barrier to inhibit the passage of microorganisms into the chamber between the tray and lid. The barrier may define a tortuous path from the outside of the container to the chamber to inhibit the passage of microorganisms. Alternatively and/or additionally the barrier may provide a seal between the tray and the lid to inhibit the passage of microorganisms. This seal may be provided various sealing materials or mechanisms such as, for example, a gasket, pliable material and/or heat sensitive material.

According to an embodiment of the invention, the lid may further include a plurality of sides having a proximal portion in communication with the central zone and a distal portion away from the central zone. In such embodiments, the lip may be defined by the distal portions of the sides. In other words, instead of the lid being relatively flat or planar, the lid may have a more three-dimensional configuration such that it has a length, width and a height. In some embodiments, the lid may have a greater height (i.e., greater three-dimensionality) than the tray.

The permeable filter provides a path for a sterilant to enter the chamber from outside the container. The permeable filter also maintains aseptic conditions inside the chamber after sterilization by allowing gases such as air to enter or exit the chamber without allow passage of microorganisms. The permeable filter is desirably located in the central portion of the lid and is located in communication with one or more openings and/or passages between the outside of the container and the chamber. However, the permeable filter and the opening(s) and/or passage(s) in communication with the filter may be located in other portions of the lid or even the tray. The permeable filter may be a conventional filter material used for sterilization container applications. It should be inexpensive enough to be discarded or recycled with the tray and the lid after a single use. Exemplary filter materials include, for example, nonwoven filter materials such as polyolefin meltblown materials and nonwoven laminate materials such as laminates of spunbond materials and meltblown materials.

The non-reusable lock is used to secure the tray and the lid together. According to the invention, the non-reusable lock includes an upper lock element forming a portion of the lid, and a lower lock element forming a portion of the tray. When the lid is mated to the tray to seal the container, the lower and upper lock elements fixedly engage into a non-reusable lock. That is, the upper and lower lock elements cannot be readily disengaged without damaging or destroying the lock and/or portions of the tray or lid. In some embodiments of the invention, the lower lock element may be formed substantially or completely out of a portion of the tray and the upper lock element may be formed substantially or completely out of a portion of the lid.

While a single non-reusable lock may be used, it may be desirable to employ multiple non-reusable locks at various locations in securing the lid and the tray together. In some embodiments of the invention, the non-reusable lock includes upper and lower lock elements that mechanically interlock to fixedly engage into a non-reusable lock to secure the lid and the tray together. The upper and lower lock elements may interlock as a tab and slot fitting such that it becomes fixedly engaged.

In some embodiments of the invention, the non-reusable lock includes lock elements that employ a material which is heat activated during steam sterilization (e.g., steam sterilization) to fixedly engage into a non-reusable lock to secure the lid and the tray together. Such heat activated material may be a shape changeable element, an adhesive, or combinations thereof. It is contemplated that the non-reusable lock may employ combinations of mechanically interlocking elements and heat activated elements. For example, a container may employ one or more different types of mechanically interlocking upper and lower lock elements (e.g., a tab and slot type lock and a bayonet type lock) such that it utilizes different mechanical types of fixedly engaged non-reusable locks. Alternatively and/or additionally, the same container could employ one or more different types of heat activated upper and lower lock elements such that it utilizes different heat activated types of fixedly engaged non-reusable locks. Moreover, the same container could employ upper and lower lock elements that combine mechanically interlocking features and heat activated features that it utilizes different hybrid (e.g., combined mechanical and heat activated) types of fixedly engaged non-reusable locks.

According to an aspect of the invention, the heat activated, shape changeable material or adhesive may be in the form of polyolefins, block copolymers, resins, waxes and combinations thereof. Desirably, these materials will have a melting point of less than 134 degrees centigrade.

The frangible release is an element that is generally more readily and easily broken or fractured than the other components of the non-reusable lock, the tray or the lid. Generally speaking, frangible release is in communication with the non-reusable lock and, upon activation, is used to irreversibly detach the non-reusable lock from only one of the tray or the lid such that the non-reusable lock remains joined to the other upon separation of the tray and lid to access the chamber after sterilization. That is, if the non-reusable lock is irreversibly detached from the tray utilizing the frangible release, the non-reusable lock remains joined to the lid. Alternatively, if the non-reusable lock is irreversibly detached from the lid utilizing the frangible release, the non-reusable lock remains joined to the tray. In an aspect of the present invention, the frangible release may be activated by travel or movement of the non-reusable lock away from the tray or lid. The frangible release may be a frangible region that is defined in or otherwise in communication with an upper lock element and/or a lower lock element and may be a plurality of frangible elements or features such as, for example, from scores, perforations, embossments, seams or combinations thereof.

In an embodiment of the present invention, the sterilization container may be configured such that: (a) the lower lock element is incorporated in the rim of the tray, (b) the upper lock element is incorporated in a peripheral portion of the lid that surrounds the central portion of the lid and includes the lip, (c) the frangible release is a frangible region defined in the lid which separates the peripheral portion of the lid from the central portion of the lid, and (d) the central portion of the lid further includes a means for removing of the central portion by activation of the frangible region. In such an embodiment, the peripheral portion of the lid and the rim of the tray fixedly engage into a non-reusable lock when the lid is mated to the tray to seal the container and activation of the frangible region irreversibly detaches the central portion of the lid while the non-reusable lock remains joined to the tray.

In yet another embodiment of the present invention, the sterilization container may be configured such that: (a) the lower lock element is incorporated in the distal portions of the sides of the tray and includes the rim of the tray, (b) the upper lock element is incorporated in a peripheral portion of the lid that surrounds the central portion of the lid and includes the lip of the lid, (c) the frangible release is a frangible region defined in the distal portions of the sides of the tray and which separates the rim of the tray from proximal portions of the sides of the tray, and (d) the distal portions of the sides of the tray further includes a means for removal of the lid and the rim of the tray by activation of the frangible region. In such an embodiment, the rim of the tray and the peripheral portion of the lid fixedly engage into a non-reusable lock when the lid is mated to the tray to seal the container and activation of the frangible region irreversibly detaches the rim from the tray while the non-reusable lock remains joined to the lid.

Generally speaking, in these embodiments, the frangible region that is defined in or otherwise in communication with the respective portions of the lid or the tray may include a plurality of frangible elements or features such as, for example, from scores, perforations, embossments, seams or combinations thereof. The means for removal of the central portion of the lid in one of the embodiments or the rim of the tray and the lid on another of the embodiments may be, for example, a hook, handle, a tab, a pull, or grip, a finger slot or the like and combinations thereof.

In an aspect of the present invention, the container may further include sterilization wrap attached to the peripheral portion of the lid and positioned in communication with a bottom side of the lid so that the sterilization wrap remains attached to the peripheral portion of the lid during irreversible detachment of the central portion of the lid and is presented for unfolding after the central portion of the lid is removed.

Generally speaking, the container may desirably be formed of, or include sections containing, a substantially transparent material adapted to withstand exposure to steam, ethylene oxide, or other forms of sterilization without degradation of the tray. This allows the contents of the container to be at least partially visible after sterilization of the container and prior to removal of the lid. Desirably, the container may be made of a recyclable material such as, for example, a thermoplastic polymeric material. Exemplary materials include, but are not limited to, polypropylene, polyethylene, polyesters and olefinic copolymers and the like. In another aspect of the invention, the material used to form the sterilization container may result in a sterilization container that is substantially rigid or may have portions of the container that are substantially rigid while other portions are less than substantially rigid or are more flexible.

The present invention also encompasses a system or method for sterilizing surgical materials. The system includes: (a) providing the non-reusable, locking sterilization container as generally described above; (b) placing surgical materials inside the non-reusable, locking sterilization container and mating the lid and the tray so the upper and lower lock elements fixedly engage into a non-reusable lock thereby securing the lid and the tray together to seal the sterilization container; (c) inserting the sterilization container into a sterilization chamber for a length of time sufficient to sterilize the surgical materials and then removing the sterilization container from the sterilization chamber; and (d) activating the frangible release in communication with the non-reusable lock to irreversibly detach the non-reusable lock from only one of the tray or the lid such that the non-reusable lock remains joined to the other upon separation of the tray and lid to access the chamber after sterilization.

According to the invention, the system may further include providing instructions and/or indicia regarding accessing the sterilized items by activating the frangible release in communication with the non-reusable lock to irreversibly detach the non-reusable lock from only one of the tray or the lid such that the non-reusable lock remains joined to the other upon separation of the tray and lid to access the chamber after sterilization. The system may also include storing the sterilization container after removal from the sterilization chamber and inspecting the non-reusable lock prior to activating the frangible release.

BRIEF DESCRIPTION OF DRAWINGS

FIGS. 27A, B and C are illustrations of certain details of exemplary upper and lower lock elements that combine mechanically interlocking features and heat activated features.

FIGS. 28A, B and C are illustrations of certain details of exemplary upper and lower lock elements in which the mechanically interlocking features and heat activated features engage the upper and lower lock elements into a non-reusable lock.

DETAILED DESCRIPTION

The present invention provides a non-reusable, locking container for sterilizing and storing surgical materials and aseptically opening and aseptically presenting surgical materials in a sterilized condition. These sterilization containers impart an increased confidence in sterility among clinicians.

The invention will be described with reference to the following description and figures which illustrate certain embodiments. It will be apparent to those skilled in the art that these embodiments do not represent the full scope of the invention which is broadly applicable in the form of variations and equivalents as may be embraced by the claims appended hereto. Furthermore, features described or illustrated as part of one embodiment may be used with another embodiment to yield still a further embodiment. It is intended that the scope of the claims extend to all such variations and embodiments.

Figure 1:
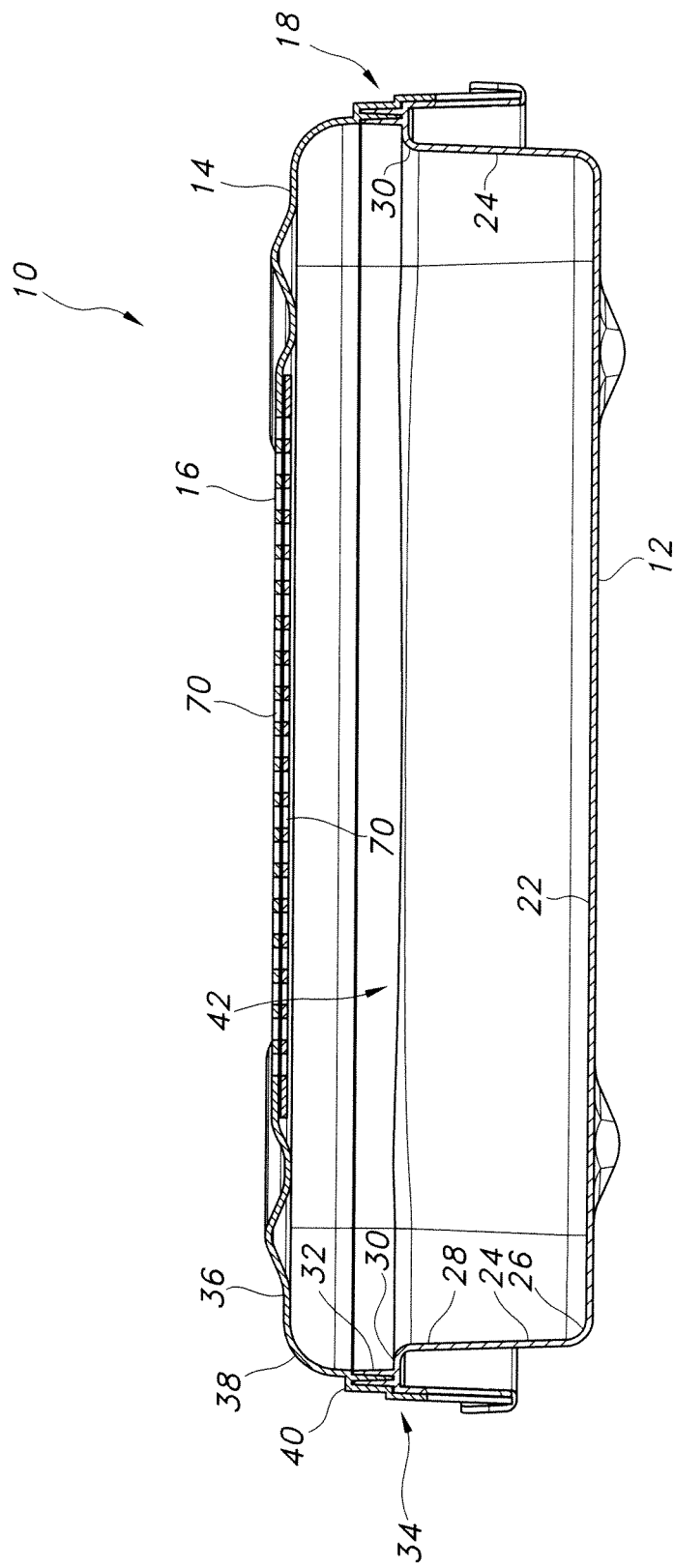
FIG. 1 is an illustration showing a cross-sectional view of an exemplary non-reusable, locking sterilization container.

Referring now to FIG. 1, there is illustrated in cross-sectional view an exemplary non-reusable, locking sterilization container 10 that includes a combination of elements that limit the container 10 to only a single sterilization cycle or single use. Generally speaking, the non-reusable, locking sterilization container 10 includes a tray 12, a lid 14, a permeable filter 16, a non-reusable lock 18 and a frangible release which is not shown in FIG. 1 but is illustrated in greater detail in FIGS. 5, 11, 13 and 14.

The tray 12 includes a base 22, a plurality of sides 24 each having a proximal portion 26 in communication with the base 22 and a distal portion 28 away from the base, and a rim 30 defined by the distal portions 28 of the sides. The rim 30 forms or includes a lower portion 32 of a barrier 34.

Figure 2:
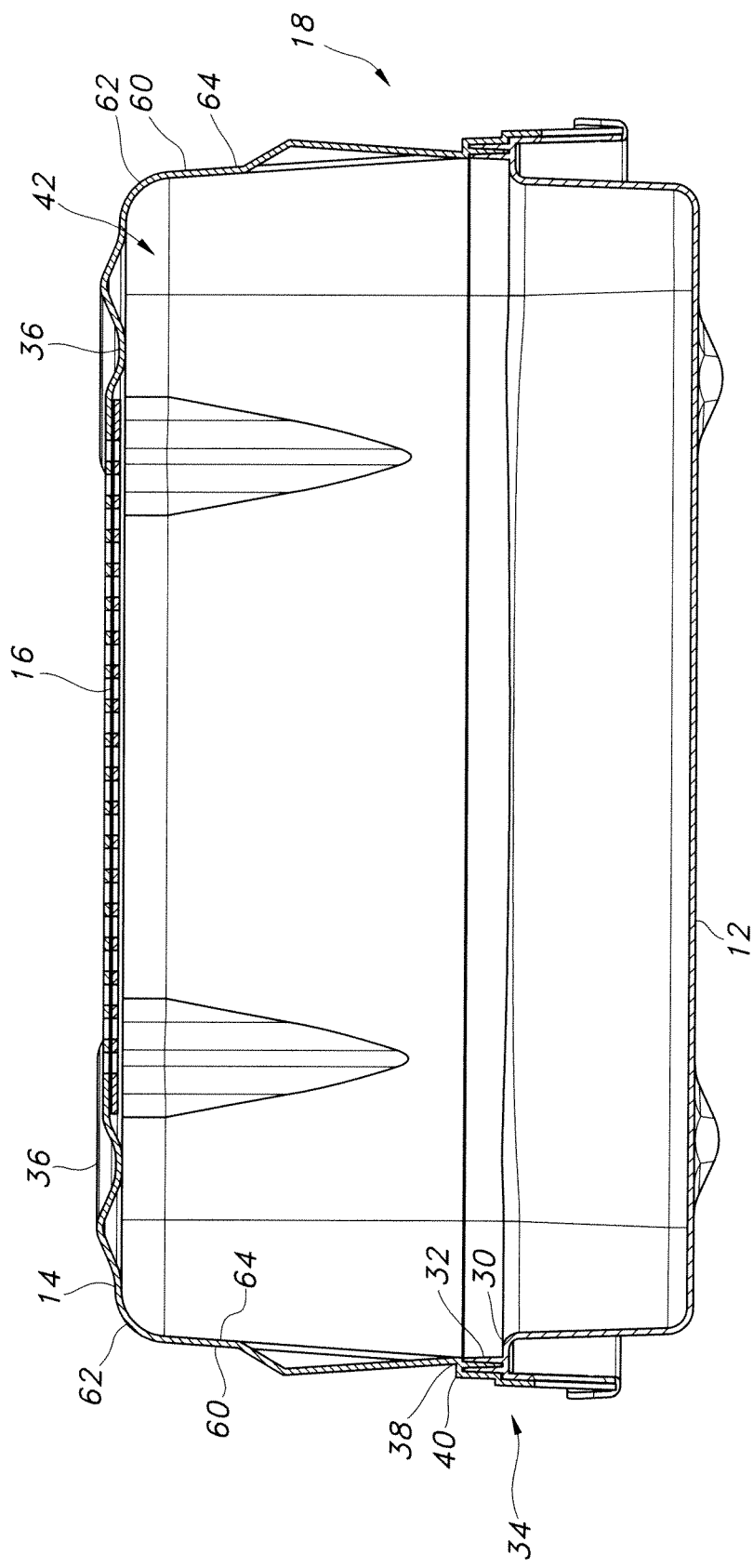
FIG. 2 is an illustration showing a cross-sectional view of an exemplary non-reusable, locking sterilization container.

The lid 14 includes a central portion 36 and a lip 38, the lip forms or includes an upper portion 40 of a barrier 34. When the lid 12 and the tray 14 are secured together, they define a chamber 42 for containing surgical materials. When the lip 38 and the rim 30 are properly secured together, they form a barrier 34 to inhibit the passage of microorganisms into the chamber 42 between the tray 12 and lid 14. The barrier 34 may desirably define a tortuous path from the outside of the container to the chamber to inhibit the passage of microorganisms as generally illustrated in FIG. 1 and FIG. 2. Alternatively and/or additionally the barrier may provide a seal between the tray and the lid to inhibit the passage of microorganisms. This seal may be provided various sealing materials or mechanisms such as, for example, a gasket, pliable material and/or heat sensitive material that is adapted to melt, deform or otherwise change shape to block to the passage of microorganisms between the tray and the lid in to the chamber.

Figure 3:
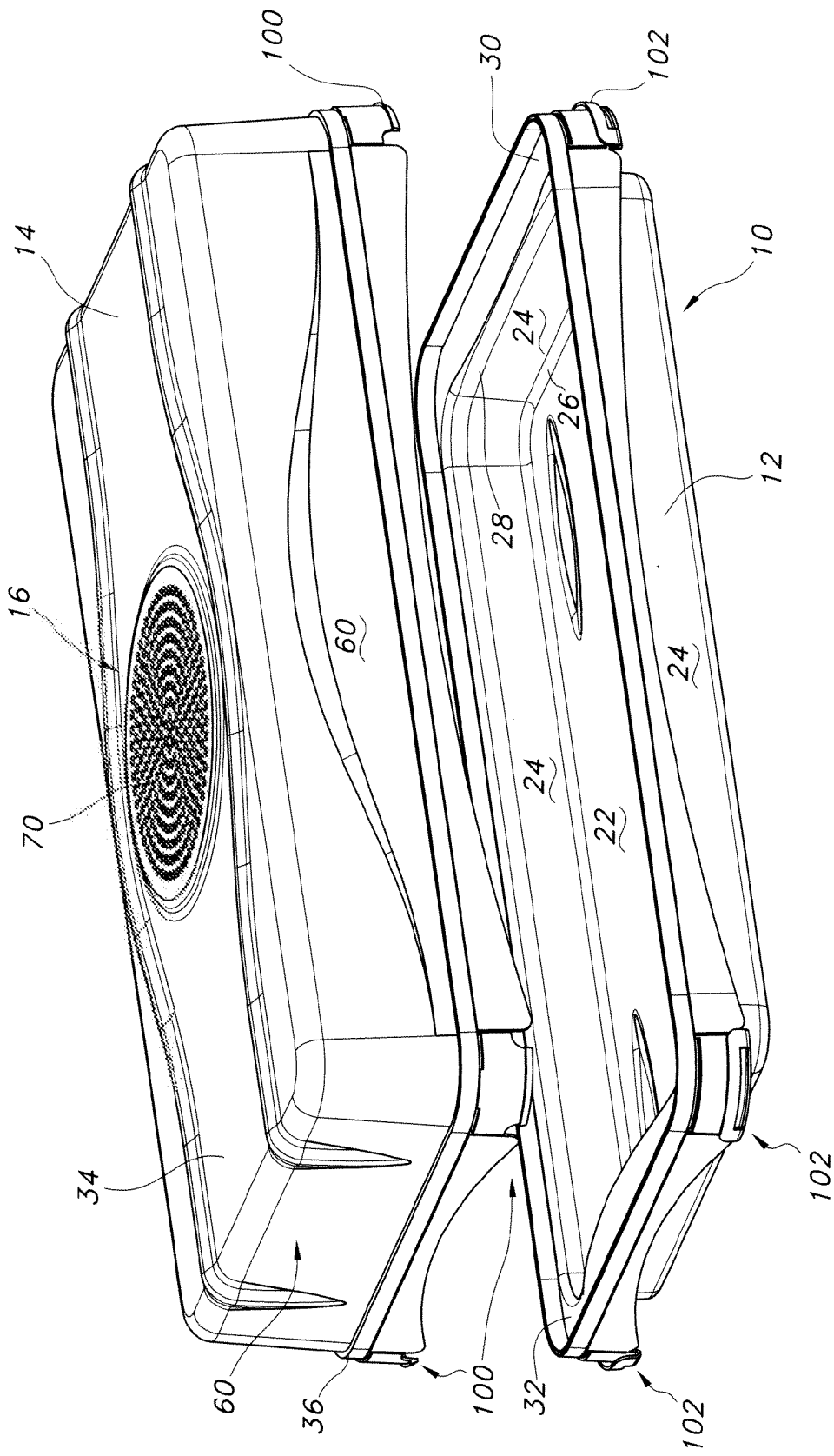
FIG. 3 is an illustration showing a perspective view of an exemplary non-reusable, locking sterilization container in which the lid and the tray are separated.

According to an embodiment of the invention, the lid 14 may further include a plurality of sides 60 having a proximal portion 62 in communication with the central portion 36 and a distal portion 64 away from the central portion 36 (which may also be referred to as a central zone 36). In such embodiments, the lip 38 may be defined by the distal portions 64 of the sides 60. In other words, instead of the lid 14 being relatively flat or planar as illustrated in FIG. 1, the lid 14 may have a more three-dimensional configuration such that it has a length, width and a height as illustrated in FIGS. 2 and 3. In some embodiments, the lid 14 may have a greater height (i.e., greater three-dimensionality) than the tray 12. For example, FIG. 2 shows this feature in a cross-sectional view of an exemplary non-reusable, locking sterilization container and FIG. 3 shows this feature in a perspective view of an exemplary non-reusable, locking sterilization container. That is, the lid has a greater height dimension than the tray.

The permeable filter 16 provides a path for a sterilant to enter the chamber 42 from outside the container 10. The permeable filter 16 also maintains aseptic conditions inside the chamber 42 after sterilization by allowing gases such as air to enter or exit the chamber without allow passage of microorganisms. The permeable filter 16 is desirably located in the central portion 36 of the lid 14 and is located in communication with one or more openings and/or passages 70 between the outside of the container 10 and the chamber 42. However, the permeable filter 16 and the opening(s) and/or passage(s) 70 in communication with the filter may be located in other portions of the lid 14 or even the tray 12. The permeable filter may be a conventional filter material used for sterilization container applications. It should be inexpensive enough to be discarded or recycled with the tray and the lid after a single use. Exemplary filter materials include, for example, nonwoven filter materials such as polyolefin meltblown materials and nonwoven laminate materials such as laminates of spunbond materials and meltblown materials.

A non-reusable lock 18 is used to secure the tray 12 and the lid 14 together. According to the invention, the non-reusable lock includes an upper lock element 100 that may form a portion of the lid 14, and a lower lock element 102 that may form a portion of the tray 12. When the lid 14 is mated to the tray 12 to seal the container, the lower and upper lock elements (100 and 102, respectively) fixedly engage into a non-reusable lock 18. That is, the upper and lower lock elements (100 and 102, respectively) engage in a manner that cannot be readily disengaged without damaging or destroying the lock and/or portions of the tray or lid rendering the lock "non-reusable". In some embodiments of the invention, the lower lock element 102 may be formed substantially or completely out of a portion of the tray 12 and the upper lock element 100 may be formed substantially or completely out of a portion of the lid 14 as illustrated in FIG. 3.

Figure 4:
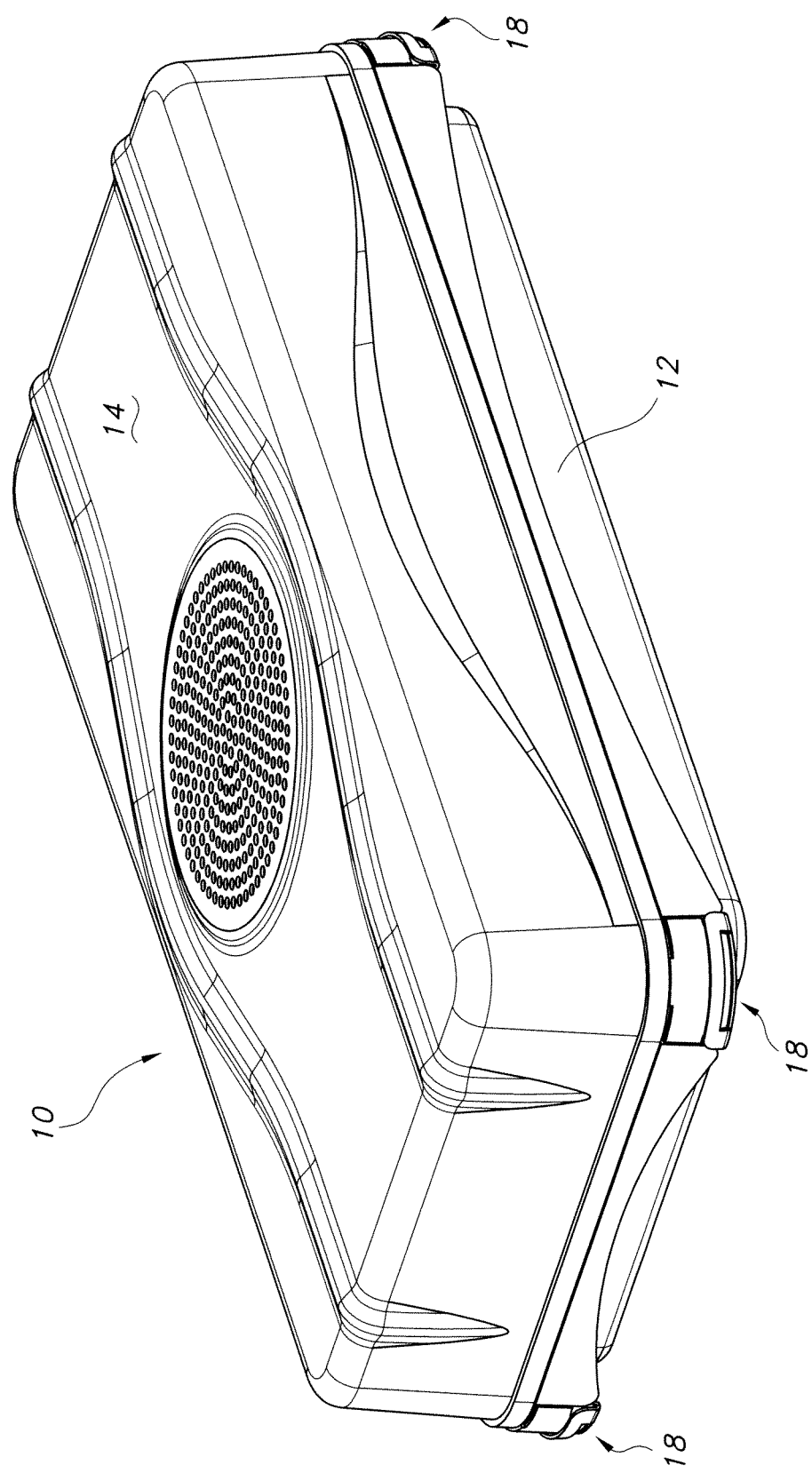
FIG. 4 is an illustration showing a perspective view of an exemplary non-reusable, locking sterilization container in which the lid and the tray are secured together.
Figure 5:
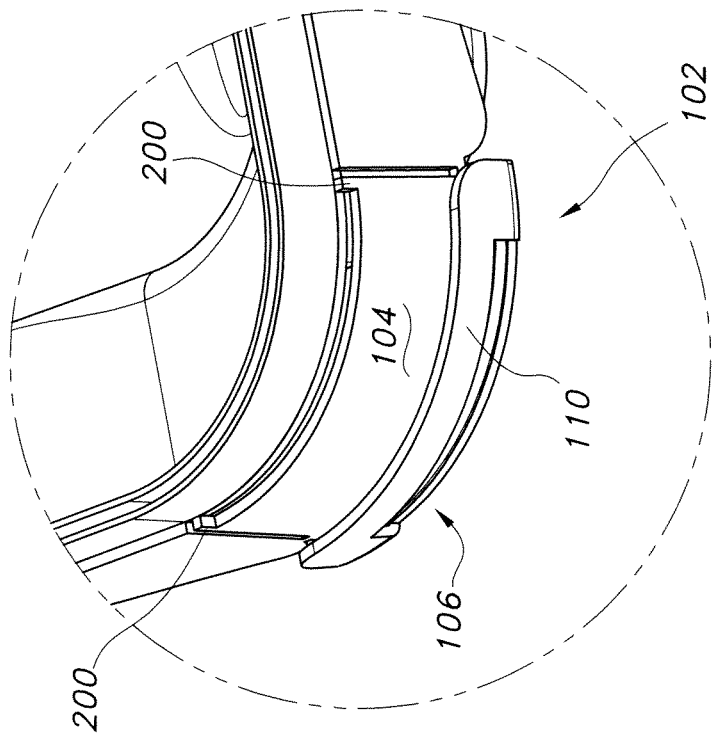
FIG. 5 is an illustration of a detail of an exemplary lower lock element of a non-reusable, locking sterilization container.

While a single non-reusable lock 18 may be used, it may be desirable to employ multiple non-reusable locks at various locations in securing the lid 14 and the tray 12 together as illustrated at, for example, FIG. 4 in which non-reusable locks 18 are present at the corners of the container 10. In some embodiments of the invention, the non-reusable lock includes upper and lower lock elements (100 and 102, respectively) that mechanically interlock to fixedly engage into a non-reusable lock to secure the lid and the tray together. The upper and lower lock elements may interlock as a tab and slot fitting such that it becomes fixedly engaged. For example, FIG. 5 illustrates a side view generally showing a lower lock element 102 which is formed into the side corner of a tray 12. Generally speaking, this lower lock element 102 is in the form of an extension 104 of the side of the tray 14 having a slot 106 defined by a rib or projection 110 of the extension 104.

Figure 6:
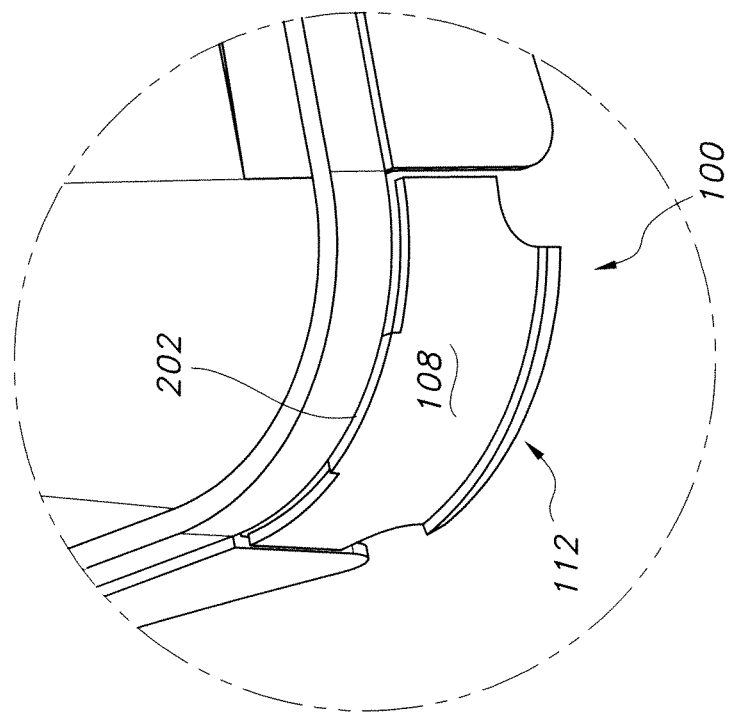
FIG. 6 is an illustration of a detail of an exemplary upper lock element of a non-reusable, locking sterilization container.
Figure 8:
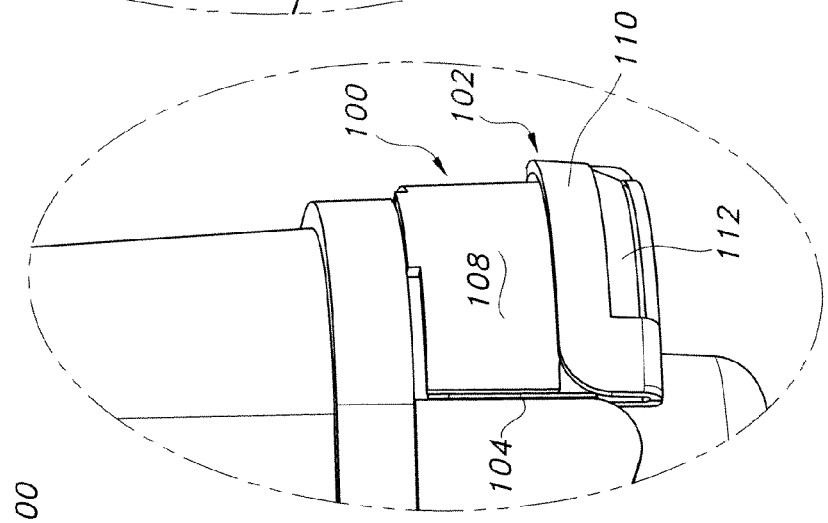
FIG. 8 is an illustration of an exemplary upper lock element and an exemplary lower lock element engaged to form a portion of an exemplary non-reusable lock.
Figure 7:
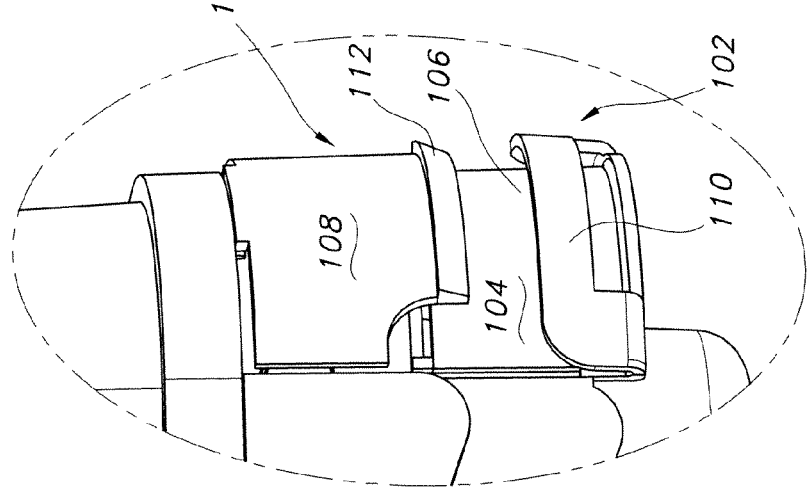
FIG. 7 is an illustration of an exemplary upper lock element and an exemplary lower lock element in alignment prior to engagement.
Figure 10:
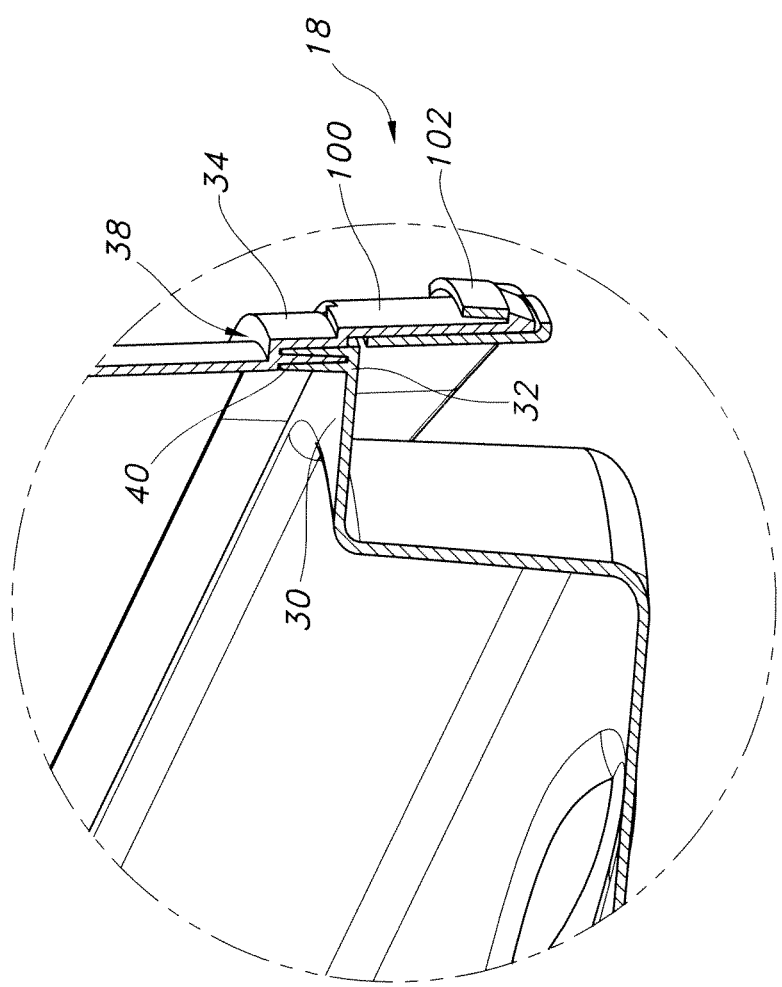
FIG. 10 is an illustration showing a cross-section of an exemplary upper lock element and an exemplary lower lock element engaged to form a portion of an exemplary non-reusable lock.

Referring to FIG. 6, there is shown in side view an upper lock element 100 in the form of a tab or bayonet extension 108 having a catch 112 that is adapted to fit into and engage the slot 106 of the lower lock element 102. An example of an embodiment of how the upper lock element 100 and lower lock element 102 may engage is illustrated in FIGS. 7 and 8. Referring to FIG. 7, an upper lock element 100 and a lower lock element 102 are aligned by bringing the lid 14 and the tray 12 together. As the lid 14 and the tray 12 are mated, the catch 112 at the end of the tab or bayonet 108 of the upper lock element 102 is introduced into the slot 106 defined by a rib or projection 110 of the extension 104 of the lower lock element 102 so that the catch 112 is engaged by the slot 106 as illustrated in FIG. 8 to form a non-reusable lock 18. FIG. 10 provides a different cross-section illustration showing the upper lock element 100 and the lower lock element 102 engaged to form a non-reusable lock.

Figure 9:
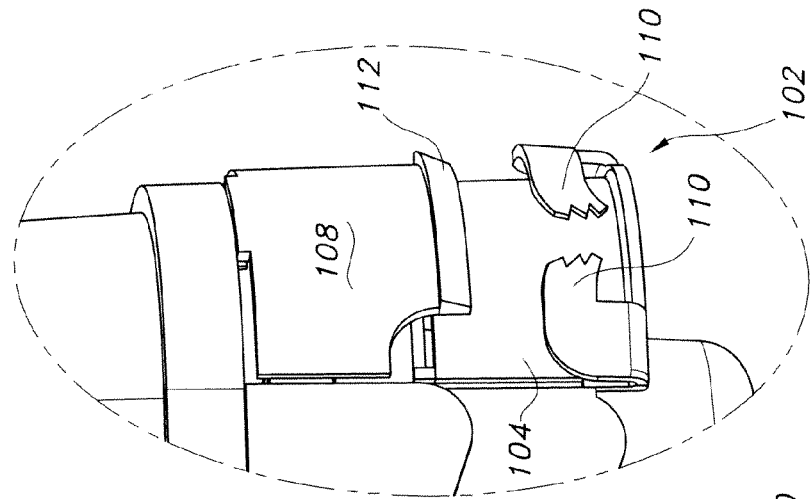
FIG. 9 is an illustration of a detail of an exemplary upper lock element and an exemplary lower lock element after engagement.

The catch 112 and/or a portion of the rib or projection 110 defining the slot 106 are configured flex or deform to allow engagement and so that the components cannot be reversed without destroying either the rib or projection 110 defining slot 106 and/or the catch 112 as illustrated in FIG. 9. Because the engagement of the upper lock element 100 and the lower lock element 102 is configured so it cannot be non-destructively disengaged by reversing the force used to engage the elements or simply pulling the lid from the tray, the contain utilizes a frangible release 200 which is an element associated with the non-reusable lock 18 that is generally more readily and easily broken or fractured than the other components of the non-reusable lock 18, the tray 12 or the lid 14. Generally speaking, frangible release 200 is in communication with the non-reusable lock 18 and, upon activation, is used to irreversibly detach the non-reusable lock 18 from only one of the tray 12 or the lid 14 such that the non-reusable lock 18 remains joined to the other upon separation of the tray 12 and lid 14 to access the chamber 42 after sterilization. That is, if the non-reusable lock 18 is irreversibly detached from the tray 12 utilizing a frangible release 200, the non-reusable lock 18 remains joined to the lid 14. Alternatively, if the non-reusable lock 18 is irreversibly detached from the lid 14 utilizing a frangible release 200, the non-reusable lock 18 remains joined to the tray 12. In an aspect of the present invention, the frangible release 200 may be activated by travel or movement of the non-reusable lock away from the tray or lid. Alternatively and/or additionally, the frangible release may be activated by twisting of the non-reusable lock.

The frangible release 200 may be a frangible region that is defined in or otherwise in communication with an upper lock element and/or a lower lock element and may be a plurality of frangible elements or features such as, for example, from scores, perforations, embossments, seams or combinations thereof.

Figure 11:
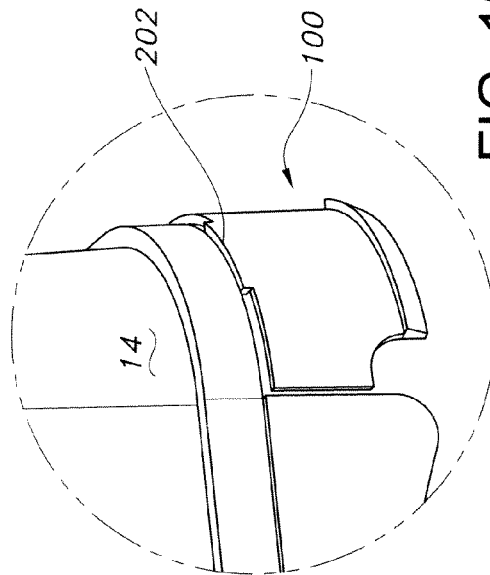
FIG. 11 is an illustration showing an exemplary frangible release associated with an exemplary lower lock element.
Figure 13:
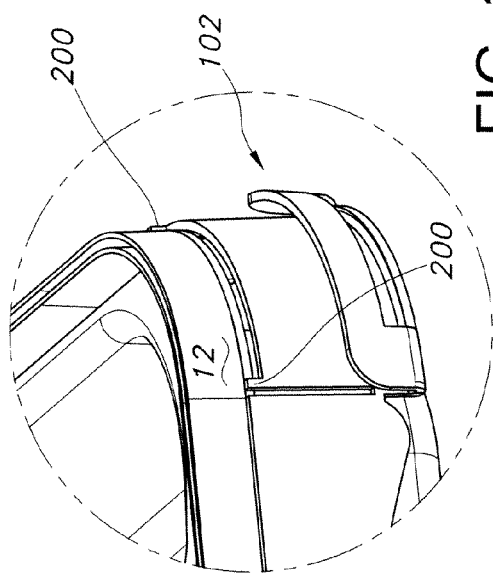
FIG. 13 is an illustration showing a side view of an exemplary upper lock element and an exemplary lower lock element engaged to form a non-reusable lock.
Figure 12:
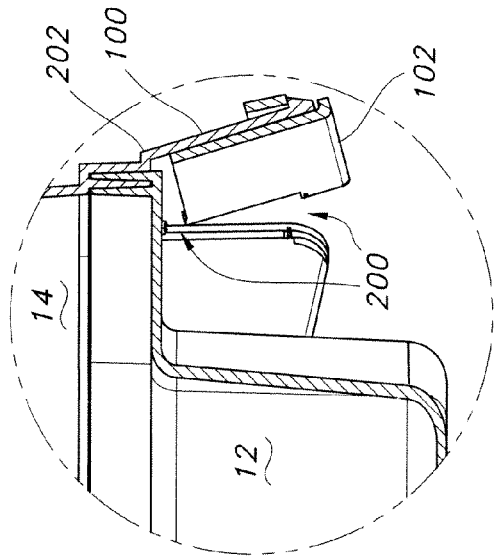
FIG. 12 is an illustration showing an exemplary hinge associated with an exemplary upper lock element.
Figure 14:
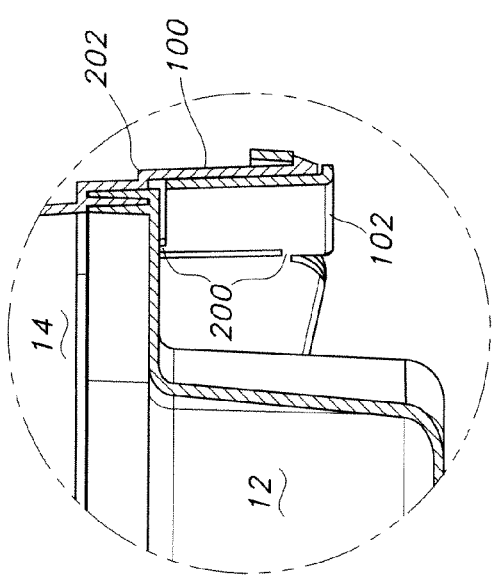
FIG. 14 is an illustration showing a side view of an exemplary non-reusable lock in which an exemplary frangible release is irreversibly detached.
Figure 15:
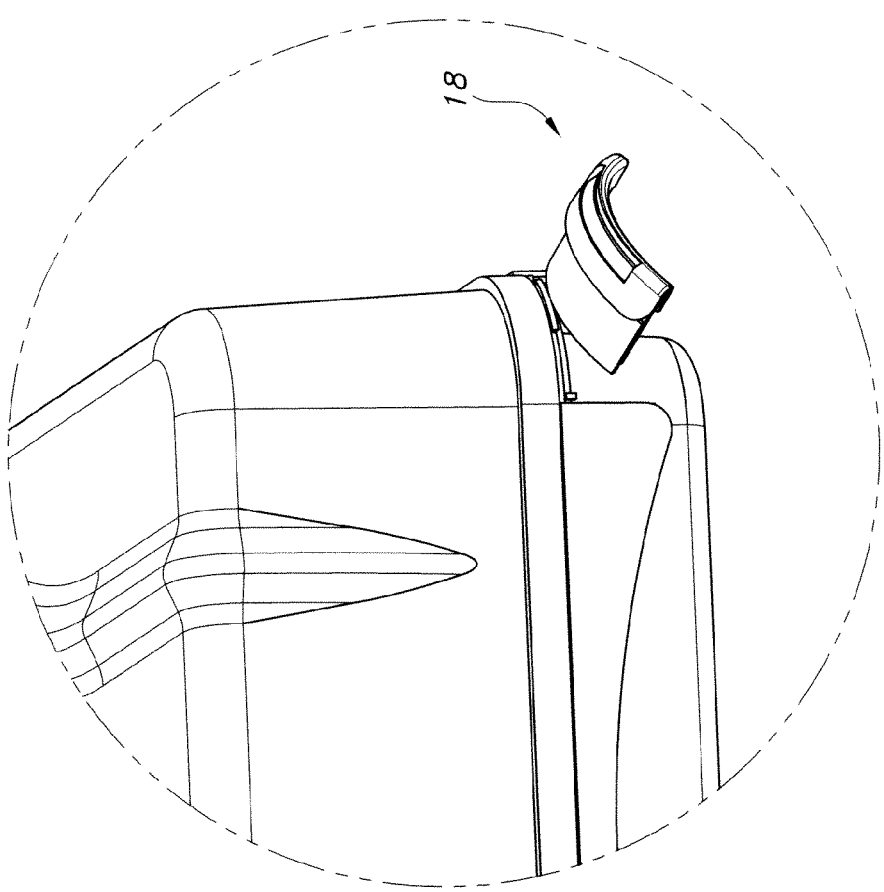
FIG. 15 is an illustration showing a perspective view of a non-reusable lock on one corner of an exemplary container after the frangible release has been activated.

Referring now to FIG. 11, a lower lock element 102 has a frangible release 200 associated with it at the location where the lower lock element 102 is connected with the tray 12. The frangible release 200 may be a series of perforations, a score line or may be a feature such as a region of thinness in the material of the lower lock element 102 at the location where it is connected with the tray 12. The corresponding upper lock element 100 is illustrated in FIG. 12 and has portion such as, for example, a living hinge 202 in the form of a thin, flexible region that allows the upper lock element 100 to bend or rotate without breaking or separating like the frangible release 200. The living hinge 202 need only be configured to bend or rotate once without breaking since the non-reusable lock is used only once. FIG. 13 is a side view illustration showing an exemplary upper lock element 100 and lower lock element 102 mated or engaged to form a non-reusable lock 18. FIG. 14 is a side view illustration showing an exemplary upper lock element 100 and lower lock element 102 mated or engaged to form a non-reusable lock 18 and in which the frangible release 200 is irreversibly broken, separated or detached at the location where the lower lock element 102 is connected with the tray 12 and the living hinge 202 associated with the upper lock element 100 has sufficient flexibility to bend and maintain attachment to the lid 14. FIG. 15 is an illustration showing a non-reusable lock 18 on one corner of the container 10 after the frangible release 200 has been activated to irreversibly detach the non-reusable lock 18 from the tray 12 while the non-reusable lock 18 remains attached to the lid 14.

Figure 16:
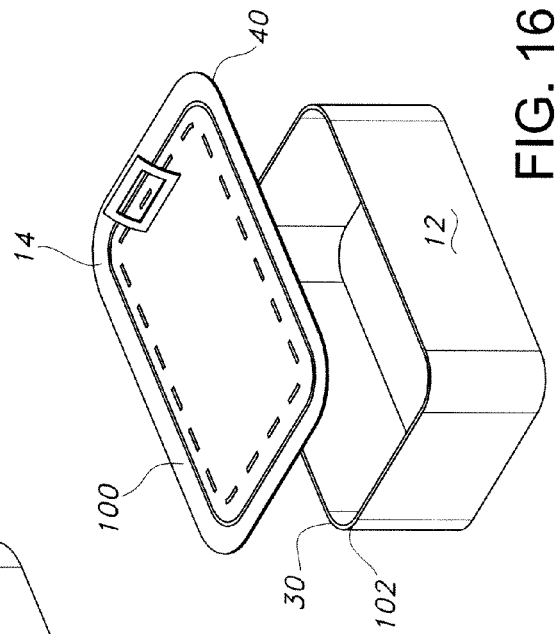
FIG. 16 is an illustration showing a perspective view of another configuration of an exemplary lower lock element and an exemplary upper lock element.
Figure 17:
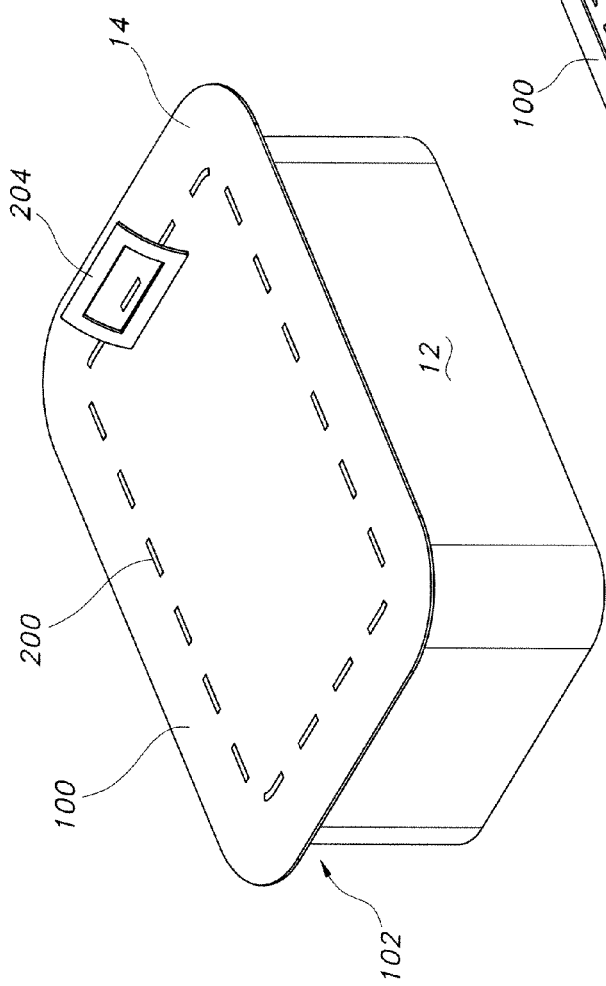
FIG. 17 is an illustration showing a perspective view of another configuration of an exemplary lower lock element and an exemplary upper lock element joined to form a non-reusable lock.
Figure 18:
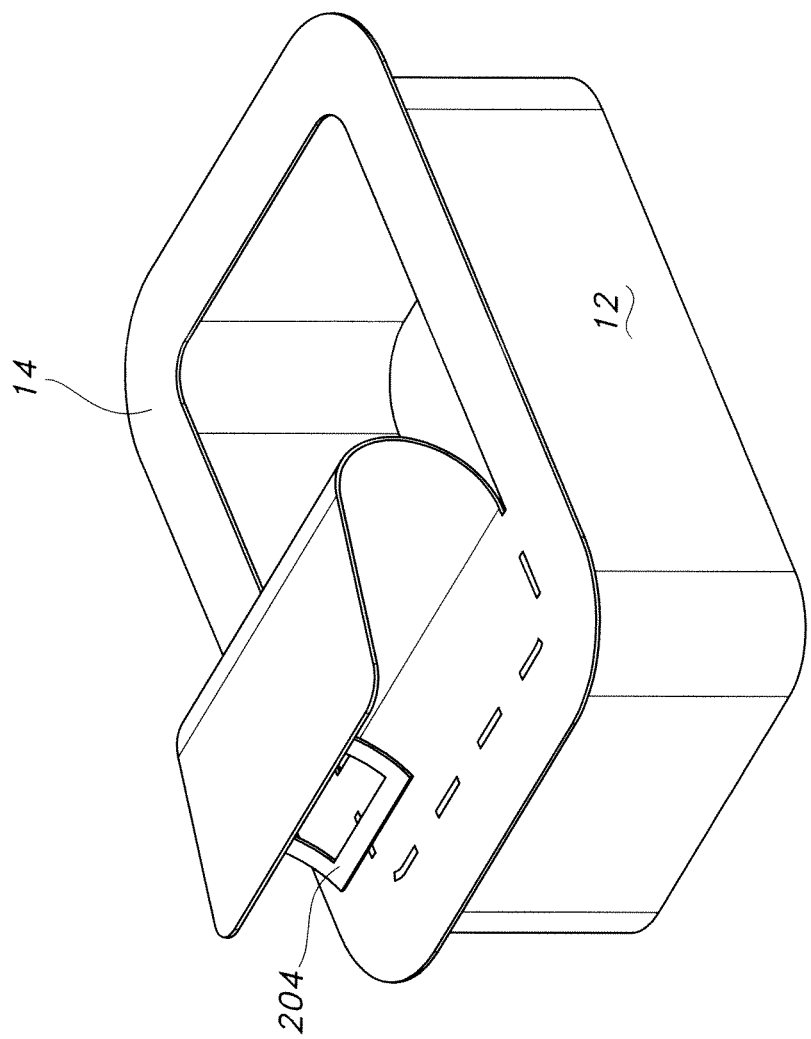
FIG. 18 is an illustration showing a perspective view of a non-reusable lock on an exemplary container after the frangible release has been activated.

In an aspect of the present invention, the sterilization container 10 may be configured such that: (a) the lower lock element 102 is incorporated in the rim of the tray 12, (b) the upper lock element 100 is incorporated in a peripheral portion of the lid 14 that surrounds the central portion of the lid and includes the lip, (c) the frangible release 200 is a frangible region 204 defined in the lid which separates the peripheral portion of the lid from the central portion of the lid, and (d) the central portion of the lid further includes a means for removing 206 of the central portion by activation of the frangible region as generally shown in FIG. 16. In such an embodiment, the peripheral portion of the lid and the rim of the tray fixedly engage into a non-reusable lock when the lid is mated to the tray to seal the container as shown in FIG. 17. Activation of the frangible region irreversibly detaches the central portion of the lid while the non-reusable lock remains joined to the tray as shown in FIG. 18.

According to the invention, the sterilization container may be configured such that: (a) the lower lock element is incorporated in the distal portions of the sides of the tray and includes the rim of the tray, (b) the upper lock element is incorporated in a peripheral portion of the lid that surrounds the central portion of the lid and includes the lip of the lid, (c) the frangible release is a frangible region defined in the distal portions of the sides of the tray and which separates the rim of the tray from proximal portions of the sides of the tray, and (d) the distal portions of the sides of the tray further includes a means for removal of the lid and the rim of the tray by activation of the frangible region. In such an embodiment, the rim of the tray and the peripheral portion of the lid fixedly engage into a non-reusable lock when the lid is mated to the tray to seal the container and activation of the frangible region irreversibly detaches the rim from the tray while the non-reusable lock remains joined to the lid.

Generally speaking, in these embodiments, the frangible region that is defined in or otherwise in communication with the respective portions of the lid or the tray may include a plurality of frangible elements or features such as, for example, from scores, perforations, embossments, seams or combinations thereof. The means for removal of the central portion of the lid in one of the embodiments or the rim of the tray and the lid on another of the embodiments may be, for example, a hook, handle, a tab, a pull, or grip, a finger slot or the like and combinations thereof.

In an aspect of the present invention, the container may further include sterilization wrap attached to the peripheral portion of the lid and positioned in communication with a bottom side of the lid so that the sterilization wrap remains attached to the peripheral portion of the lid during irreversible detachment of the central portion of the lid and is presented for unfolding after the central portion of the lid is removed.

Generally speaking, the container may desirably be formed of, or include sections containing, a substantially transparent material adapted to withstand exposure to steam, ethylene oxide, or other forms of sterilization without degradation of the tray. This allows the contents of the container to be at least partially visible after sterilization of the container and prior to removal of the lid. Desirably, the container may be made of a recyclable material such as, for example, a thermoplastic polymeric material. Exemplary materials include, but are not limited to, polypropylene, polyethylene, polyesters, certain thermoplastic polyurethanes, olefinic copolymers and the like. In another aspect of the invention, the material used to form the sterilization container may result in a sterilization container that is substantially rigid or may have portions of the container that are substantially rigid while other portions are less than substantially rigid or are more flexible. While portions of the container may be flexible, it is necessary that the container have sufficient rigidity that at least one container may be stacked on top of another container during storage at normal storage room temperatures which may range from about 60° F. to about 85° F. Desirably, the container may have sufficient rigidity that at least one container may be stacked on top of another container during heat sterilization conditions at temperatures greater than about degrees 273° F. (134° C.).

In some embodiments of the invention, the non-reusable lock 18 includes lock elements that employ a material which is heat activated during sterilization (e.g., steam sterilization) to fixedly engage into a non-reusable lock to secure the lid and the tray together. Such heat activated material may be a shape changeable element, an adhesive, or combinations thereof. According to the invention, the heat of steam sterilization provides the energy source necessary to melt, soften, deform or to induce deformation of the shape of at least one element involved in engaging lock components together. Examples of deformation that may be used to engage lock components together include, but are not limited to, melting, plastic flow, shrinkage, warping, expansion, twisting, kinking, and melding. Accordingly, a shape changeable element is an element that melts, softens, or otherwise deforms under the heat of sterilization, and more desirably, the level of heat provided by steam sterilization so that the element flows, shrinks, sags, warps, expands twists, kinks, melds or bonds to engage lock components together.

Suitable shape changeable elements for inclusion in lock components that engage are made from thermoplastic materials, specifically those with Ball & Ring Softening Points (i.e., Ball & Ring Melt Points) as determined in accordance with ASTM E28 in a range from about 135° F. (59° C.) to about 300° F. (149° C.). For example, the materials may have Ball & Ring Softening Points (i.e., Ball & Ring Melt Points) as determined in accordance with ASTM E28 between about 266° F. (130° C.) and about 300° F. (149° C.). As another example, the materials may have Ball & Ring Softening Points (i.e., Ball & Ring Melt Points) as determined in accordance with ASTM E28 at or below 273° F. (134° C.). The Ball and Ring Softening Point is a method of determining the softening point of thermoplastics. Generally speaking, a specimen is cast or molded inside a ring of metal with an inside diameter of about 16 mm and dimension of about 2.4 mm thick by about 6.4 mm deep. This ring is placed above a metal plate in a fluid heating bath (~1 gm/cc liquid bath), and a 9.5 mm diameter steel ball weighing 3.5 grams is placed in the center of the specimen. The softening point is considered to be the temperature of the fluid when the ball penetrates the specimen and touches the lower plate. The test can be automated and may be conducted with equipment such as a Ring And Ball Automatic Softening Point Tester available from Mastrad Ltd of Douglas, United Kingdom (Catalog Number 10036000 Automatic Ring & Ball Tester Model D36-EN1427) or a Petrotest® RK5A Softening Point Tester available from Petrotest® Instruments GmbH & Co. KC of Dahlewitz, Germany—generally in accordance with ASTM D36 or ASTM E28.

Generally speaking, such materials are solids that resist force-induced deformation at room and ambient storage temperatures. As they approach their Ball & Ring Softening Points, these materials dimensionally deform in response to applied forces. The requirement that suitable thermoplastic materials for use as shape changeable elements have Ball & Ring Softening Points at or below 273° F. (134° C.) ensures that heat, time, and other environmental conditions typical of steam sterilization will provide the necessary missing amounts of energy to induce transformation of the shape changeable elements in the lock components from their pre-sterilization shape to another shape that promotes engagement of contacting lock components. After sufficient heat dissipation at the conclusion of the sterilizing step, the transformed shape changeable element solidifies into a final shape.

According to an aspect of the invention, the heat activated, shape changeable material or adhesive may be in the form of polyolefins, block copolymers, resins, waxes and combinations thereof. Desirably, these materials will have a melting point below 273° F. (134° C.). One category of thermoplastic materials suitable for use as the shape changeable elements are hot melt adhesives. Examples of specific hot melt adhesives that comply with the Ball & Ring Softening Point criteria, can form acceptable pre-sterilization shape changeable elements, and can transform during steam sterilization into desirable final shapes are thermoplastic hot melt adhesives 3796; 3792; 3789; 3764; 3762; 3750; 3747; 3738; 3794; 3798LM; 3792LM; 3776LM; 3762LM; 3755LM; 3750LM; 6111HT; and 6116 available from 3M Company of St. Paul, Minn. It is contemplated that these materials may have an associated color or other additive that aids in quick determination of appropriate heat activation and lock component engagement.

It is contemplated that the non-reusable lock 18 may employ combinations of mechanically interlocking elements and heat activated elements. For example, a container may employ one or more different types of mechanically interlocking upper and lower lock elements (e.g., a tab and slot type lock) such that it utilizes different mechanical types of fixedly engaged non-reusable locks. Alternatively and/or additionally, the same container could employ one or more different types of heat activated upper and lower lock elements such that it utilizes different heat activated types of fixedly engaged non-reusable locks. Moreover, the same container could employ upper and lower lock elements that combine mechanically interlocking features and heat activated features that it utilizes different hybrid (e.g., combined mechanical and heat activated) types of fixedly engaged non-reusable locks.

Figure 19:
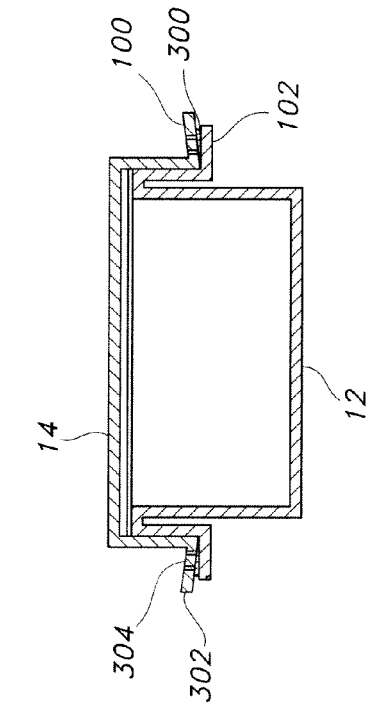
FIG. 19 is an illustration showing a cross-sectional view of an exemplary container in which exemplary lower lock elements also include a heat-activated shape changeable element.
Figure 20:
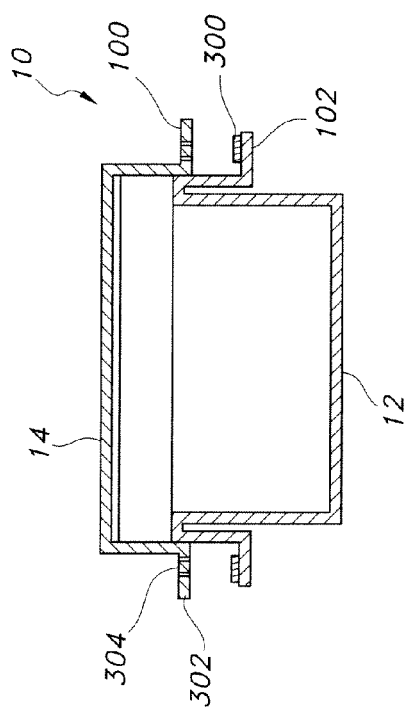
FIG. 20 is an illustration showing a cross-sectional view of an exemplary container showing a detail of the respective upper and lower lock elements.
Figure 21:
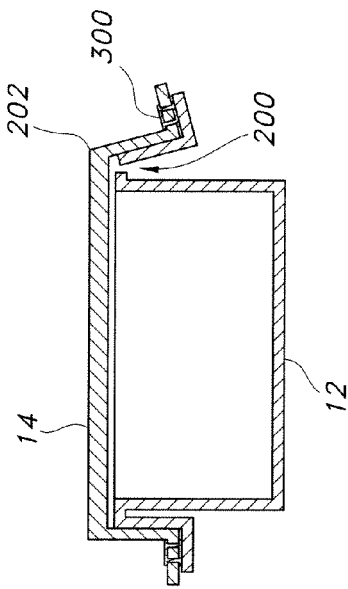
FIG. 21 is an illustration showing a cross-sectional view of an exemplary container in which successful heat activation of shape changeable elements.

Referring now to FIGS. 19-21, the non-reusable lock may include lock elements that employ a material which is heat activated during sterilization to fixedly engage into a non-reusable lock to secure the lid and the tray together. More particularly, FIGS. 19-21 are illustrations showing a cross-sectional view of container 10 with a lid 14 and its respective upper lock elements 100 and a tray 12 with its respective lower lock elements 102 and their relative positioning before closing, before heat activation of the lock components and during opening. FIGS. 19-21 illustrate an example in which a shape changeable element 300 that is heat activated such that it deforms and changes shape is configured to directly engage the lock elements 100 and 102 together and provide visual and tactile cues regarding the engagement of the non-reusable lock.

FIG. 19 shows an initial cross-sectional illustration of a container 10 with a lid 14 and its respective upper lock elements 100 and a tray 12 with its respective lower lock elements 102 and which also has a shape changeable element 300 attached to the lower lock elements 102. The upper lock elements 100 are part of the lid 14 and are on a periphery 302 of the lid 14 and may be in the form of apertures 304 defined by the material of the periphery 302 of the lid. The lid and tray and respective lock elements are positioned to align the respective lock elements for subsequent contact with each other. Features such as, for example, the barrier 34 formed by portions of the lip of the lid and rim of the tray are not illustrated.

FIG. 20 shows the lid 14 closed on the tray 12 with their respective lock elements 100 and 102 in contact with each other but without successful engagement of the lock elements. Portions of the periphery 302 of the lid 14 deflect due to contact of the respective lock elements 100 and 102. The deflection establishes a visual and tactile cue that engagement of the lock elements has not occurred. This deflection illustrates that the force of the upper lock element 100 against the lower lock element 102 as well as the force of gravity are insufficient to accomplish successful engagement of the upper and lower lock elements.

FIG. 21 shows the results of successful heat activation of one or more shape changeable elements 300 such that it deforms and changes shape to directly engage the lock elements 100 and 102 together and provide visual and tactile cues regarding the engagement of the non-reusable lock. Heat applied over time from the sterilization cycle adds to the forces generated by the deflection of the upper lock element 100 to engage the upper lock element with the lower lock element 102. In contrast with the corresponding positions of FIG. 20, the one or more shape changeable elements 300 of the lower lock elements 102 have deformed in and through the apertures of the upper lock elements 100. The final shape of the shape changeable elements 300 is visible in the apertures 304 and, by filling the apertures 304, is tactilely apparent. The previous deflections of the peripheral portions 302 of the lid 14 have abated; these changes contribute additional visual and tactile cues indicating that the upper lock elements 100 and the lower lock elements 102 are engaged to form a non-reusable lock 18. With dissipation of the heat and setting or hardening of the shape changeable elements 300, a final shape is achieved, effectively joining the lid 14 and the base 12 to form a container 10. Depending on the type of materials selected for the shape changeable element 300, the engagement may be mechanical/structural in nature, the engagement may be primarily adhesive in nature, or the engagement may have both aspects present.

Figure 22:
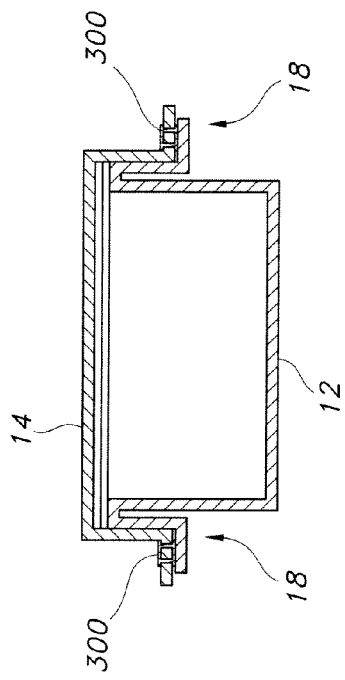
FIG. 22 is an illustration showing a cross-sectional view of the irreversible detachment of a frangible release.

FIG. 22 is an illustration showing the irreversible detachment of a frangible release 200 located at the interface between the lower lock element 102 and the tray 12. The failure occurs as the result of an application of forces to open the container 10. Irreversible detachment of the frangible release 200 also provides an additional tactile cue concerning engagement of the upper lock element 100 and the lower lock element 102 into a non-reusable lock 18. In contrast to FIG. 19, irreversible detachment of the frangible release 200 results in the non-reusable lock 18 being clearly attached to the lid 14 by way of the upper lock element 100 through the living hinge 202 the engaged lock components thus creating a distinctly different lid and base set. That is, the lid 14 with its respective upper lock elements 100 and the tray 12 with its respective lower lock elements 102 that are brought together as shown in FIG. 19 to form the container 10 prior to heat activation are different from the lid 14 with the attached non-reusable lock 18 containing the upper lock elements 100, the lower lock elements 102 and the shape changeable element 300 that is separated from the tray 12 which no longer has the lower lock elements 102 that were irreversibly detached at the frangible release 200.

Figure 23:
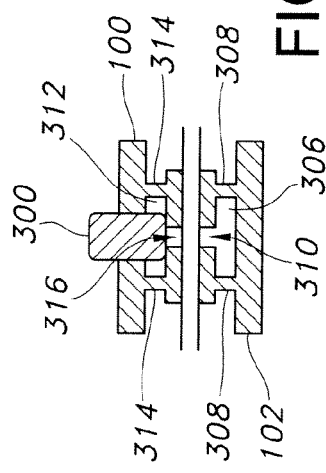
Figure 24:
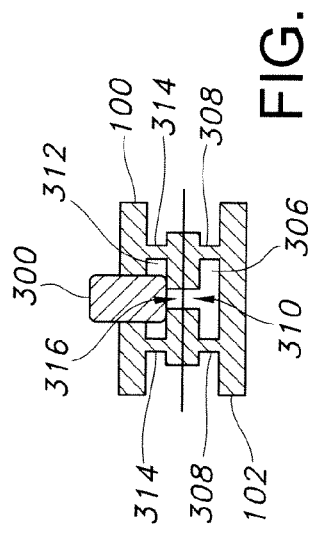
FIG. 24 is an illustration showing a cross-sectional view of another detail of an exemplary lower lock element and an exemplary upper lock element.
Figure 25:
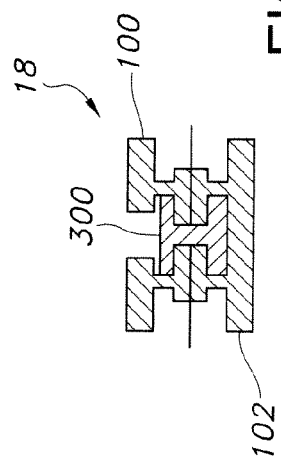
FIG. 25 is an illustration showing a cross-sectional view of another detail of an exemplary lower lock element and an exemplary upper lock element that have been engaged to form a non-reusable lock.

FIGS. 23-25 represent cross-sectional illustrations of a specific detail of a combination of upper lock elements 100 and lower lock elements 102 having a different configuration than those illustrated in FIGS. 19-22. The tray 12 and lid 14 (not shown) each have respective lower lock elements 102 and upper lock elements 100. Each lower lock element 102 defines a lower cavity 306 in which walls 308 define an aperture 310 and each upper lock element 100 defines an upper cavity 312 in which walls 314 define an aperture 316. The aperture 310 of the lower cavity 306 and the aperture 316 of the upper cavity 312 align and are in communication when positioned against each other. FIG. 23 shows a small detail of the lower lock element 102 and upper lock element 100 aligned for subsequent contact such that the aperture 310 of the lower cavity 306 and the aperture 316 of the upper cavity 312 align. In this configuration; the upper lock element 100 holds the shape changeable element 300 so that it visibly and tactilely protrudes from the upper lock element. FIG. 24 shows the lower lock element 102 and upper lock element 100 aligned such that the aperture 310 of the lower cavity 306 and the aperture 316 of the upper cavity 312 are in communication. In this configuration, gravity becomes a significant factor in carrying out successful engagement of the upper and lower lock elements as the shape changeable element 300 is configured to melt and flow.

Referring now to FIG. 25, there is shown a cross-sectional illustration of the lower lock element 102 and upper lock element 100 that have been engaged to form a non-reusable lock 18. After a sufficient amount of heat is provided to make the shape changeable element 300 fluid-like, the shape changeable element 300 deforms downwards into the upper cavity 312 and through the aligned apertures 316 and 310 into the lower cavity 306. After heat is dissipated and the shape changeable element 300 is hardened into a new shape defined by the walls of the cavities 306 and 312 and the apertures 310 and 316, the respective upper and lower lock components 100 and 102 are engaged into a non-reusable lock 18. Depending on the type of materials selected for the shape changeable element 300, the engagement may be mechanical/structural in nature, the engagement may be primarily adhesive in nature, or the engagement may have both aspects present. The recess of the final shape contrasts with its initial position and provides visual and tactile cues that engagement has occurred and that any contents within the container should be sterile because the sterilization conditions were required to change the shape of the shape changeable element 300.

Figure 26:
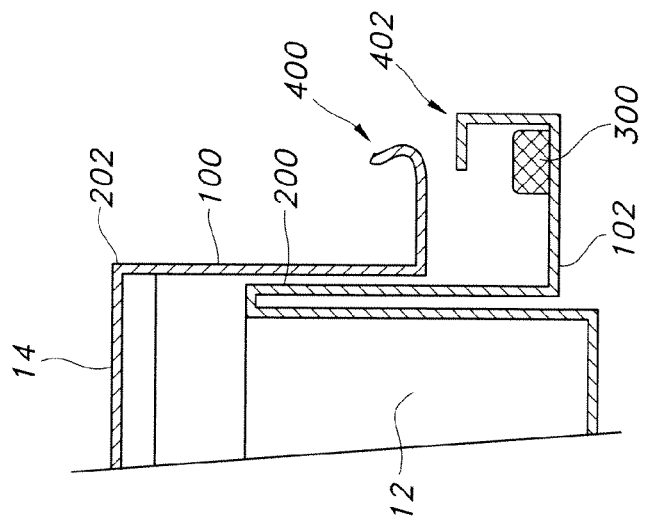
FIG. 26 is an illustration showing a cross-sectional view of another exemplary upper lock element and exemplary lower lock element having structural features that are designed to interlock.

Other embodiments are contemplated in which the lock components of lids and trays may be engaged successfully regardless of the container orientation with respect to gravity. For example, FIG. 26 is an illustration of one such configuration. In this configuration, the upper lock element 100 and the lower lock element 102 have structural features that are designed to interlock and utilize a shape changeable element 300 having relatively strong adhesive qualities. The upper lock element 100 has a peripheral lip portion 400 that is flexible. The lower lock element which connects to the tray 12 by way of a frangible release 200 includes a channel feature 402 that partially obscures a shape changeable element 300. The frangible release 200 of the lower lock component 102 is less flexible than the living hinge 202 of the upper lock component. FIG. 26 shows the lid and tray and respective components properly aligned for subsequent contact of the lock components.

Generally speaking, when the lid and tray are positioned so that their lock elements contact with each other, the peripheral lip portion 400 of the upper lock element 100 deflects in response to the channel feature 402 and the shape changeable element 300 of the lower lock element 102.

As heat is applied during the sterilization cycle, heat-induced deformation of the shape changeable element 300 and the spatial change in the peripheral lip portion 400 allows the upper lock element 100 to seat within the channel feature 402 of the lower lock element. This seating of the peripheral lip portion 400 within the channel feature 402 of the lower lock element provides a visual cue about the engagement state. Once the heat from the sterilization cycle dissipates, the shape changeable element 300 achieves its final shape and its adhesive qualities ensure that the seated position of the peripheral lip portion 400 within the channel feature 402 is maintained at opening forces that cause the frangible release 200 to allow the lower lock element 102 to irreversibly detach from the tray 12.

In an aspect of the present invention, the shape changeable element 300 may be subject to an applied mechanical force such as, for example, a compressive force such as a spring under tension, a metal band or other element that provides resistance to compression. When heat sterilization conditions provide sufficient heat for the shape changeable element 300 to deform, the applied mechanical force (e.g., compressive force) may displace the shape changeable element 300 so that the upper lock element and the lower lock element are engaged to form a non-reusable lock. Desirably, the transformation of the shape changeable element into a final shape after the heat of steam sterilization and the compressive forces have dissipated results in a configuration in which the final shape protrudes into voids, cavities or other structures of each upper and lower lock element forming the physical engagement of the lock elements and also providing visual and tactile cues that lock engagement and steam sterilization conditions have occurred.

It is also contemplated that the design of the upper and lower lock elements and the shape changeable elements can be configured so that engagement of the lock elements takes place without obvious dimensional changes. Without a visually obvious difference in its final shape, an additional element, a color change element is desirably included in at least one lock element and is visible from an external vantage point. For example, the upper lock element may include a color change element that is visible externally upon activation and which also forms part of the structure of the lock element, shown as the cover material, which partially encloses this lock component's shape changeable element. This arrangement may involve engagement via cohesive and adhesive forces. An equally feasible alternative to this arrangement is to rely on engagement only through adhesive forces that are generated by or increased through steam sterilization conditions. For example, the lower lock element may lack a shape changeable element but a shape changeable element may be integrated in the upper lock element. Engagement is achieved by adhesion between the surface of the lower lock element and the shape changeable element integrated in the upper lock element. Alternatively and/or additionally, a shape changeable element may be integrated in both the upper and lower lock elements and engagement is achieved by adhesion between the shape changeable elements integrated in both the upper lock element and the lower lock element.

Referring now to FIGS. 27A-C, there is illustrated certain details of upper and lower lock elements that combine mechanically interlocking features and heat activated features (i.e., combined mechanical and heat activated features) that permit the upper and lower lock elements to fixedly engage into a non-reusable lock. FIG. 27A illustrates a perspective view of an upper lock element 100 in the form of a tab or bayonet extension 108 having a catch 112 that is fitted into and reversibly engaged with the slot 106 defined by the shape changeable element in the form of a rib or projection 110 of the lower lock element 102 prior to heat activation of that rib or projection 110.

An example of an embodiment of how the upper lock element 100 and lower lock element 102 are engaged prior to heat activation is illustrated in FIGS. 27B and 27C. FIG. 27B is an illustration showing a perspective view of a portion of an upper lock element and a lower lock element that were brought together so the catch 112 at the end of the tab or bayonet 108 of the upper lock element is introduced into the slot 106 defined by a shape changeable rib or projection 110 of the lower lock element so that the catch 112 is engaged by the slot 106. FIG. 27C is an illustration showing a perspective view of a detail of how the upper and lower lock elements may be disengaged prior to heat activation of the shape changeable rib or projection 110. In FIG. 27C, it can be seen that the slot 106 defined by the shape changeable rib or projection 110 is sufficiently large to allow flexing of the tab or bayonet 108 so that the catch 112 can be brought behind the shape changeable rib or projection 110 prior to heat activation so that the combination of the upper lock element 100 and the lower lock element 102 do not yet form a non-reusable lock.

FIGS. 28A-C provides certain details of upper and lower lock elements in which the mechanically interlocking features and heat activated features (i.e., combined mechanical and heat activated features) fixedly engage the upper and lower lock elements into a non-reusable lock. FIG. 28A illustrates a perspective view of an upper lock element 100 in the form of a tab or bayonet extension 108 having a catch 112 that is fitted into and fixedly engaged with the narrowed slot defined by the shape changeable rib or projection 110 of the lower lock element 102 after heat activation. That is, the shape changeable rib or projection 110 is deformed, curled, sagged or otherwise altered by heat activation so it narrows the dimensions of the slot 106 such that the clearance between the catch 112 and the rib or projection 110 is insufficient for the upper lock element 100 to be released from the lower lock element 102 without destroying the two components.

Further detail of how the upper lock element 100 and lower lock element 102 are engaged after heat activation is illustrated in FIGS. 28B and 28C.

FIG. 28B is an illustration showing a perspective view of a portion of an upper lock element and a lower lock element after heat activation. As can be seen, the shape changeable rib or projection 110 has been altered by heat activation such that the catch 112 at the end of the tab or bayonet 108 of the upper lock element is fixedly engaged in the slot 106 defined by shape changeable rib or projection 110. FIG. 28C is an illustration showing a perspective view of the elements after heat activation of the rib or projection 110. In FIG. 28C, the tab or bayonet 108 has been flexed but the deformation of the shape changeable rib or projection 110 resulting from heat activation is large enough that the catch 112 cannot be brought behind the rib or projection 110. As a result, the combination of the upper lock element 100 and the lower lock element 102 are fixedly engaged to form a non-reusable lock.

Of course, other configurations are contemplated. For example, the tab or bayonet 108 may be a shape changeable tab or bayonet which is heat activated so it deforms in a manner that fixedly engages the upper lock element and the lower lock element into a non-reusable lock. As another example, the tab or bayonet 108 and rib the or projection 110 may each be a shape changeable element that is heat activated so they deform together in a manner that fixedly engages the upper lock element and the lower lock element into a non-reusable lock.

The present invention also encompasses a system or method for sterilizing surgical materials. The system includes: (a) providing the non-reusable, locking sterilization container as generally described above; (b) placing surgical materials inside the non-reusable, locking sterilization container and mating the lid and the tray so the upper and lower lock elements fixedly engage into a non-reusable lock thereby securing the lid and the tray together to seal the sterilization container; (c) inserting the sterilization container into a sterilization chamber for a length of time sufficient to sterilize the surgical materials and then removing the sterilization container from the sterilization chamber; and (d) activating the frangible release in communication with the non-reusable lock to irreversibly detach the non-reusable lock from only one of the tray or the lid such that the non-reusable lock remains joined to the other upon separation of the tray and lid to access the chamber after sterilization.

According to the invention, the system may further include providing instructions and/or indicia regarding accessing the sterilized items by activating the frangible release in communication with the non-reusable lock to irreversibly detach the non-reusable lock from only one of the tray or the lid such that the non-reusable lock remains joined to the other upon separation of the tray and lid to access the chamber after sterilization. The system may also include storing the sterilization container after removal from the sterilization chamber and inspecting the non-reusable lock prior to activating the frangible release.

Figure 29:
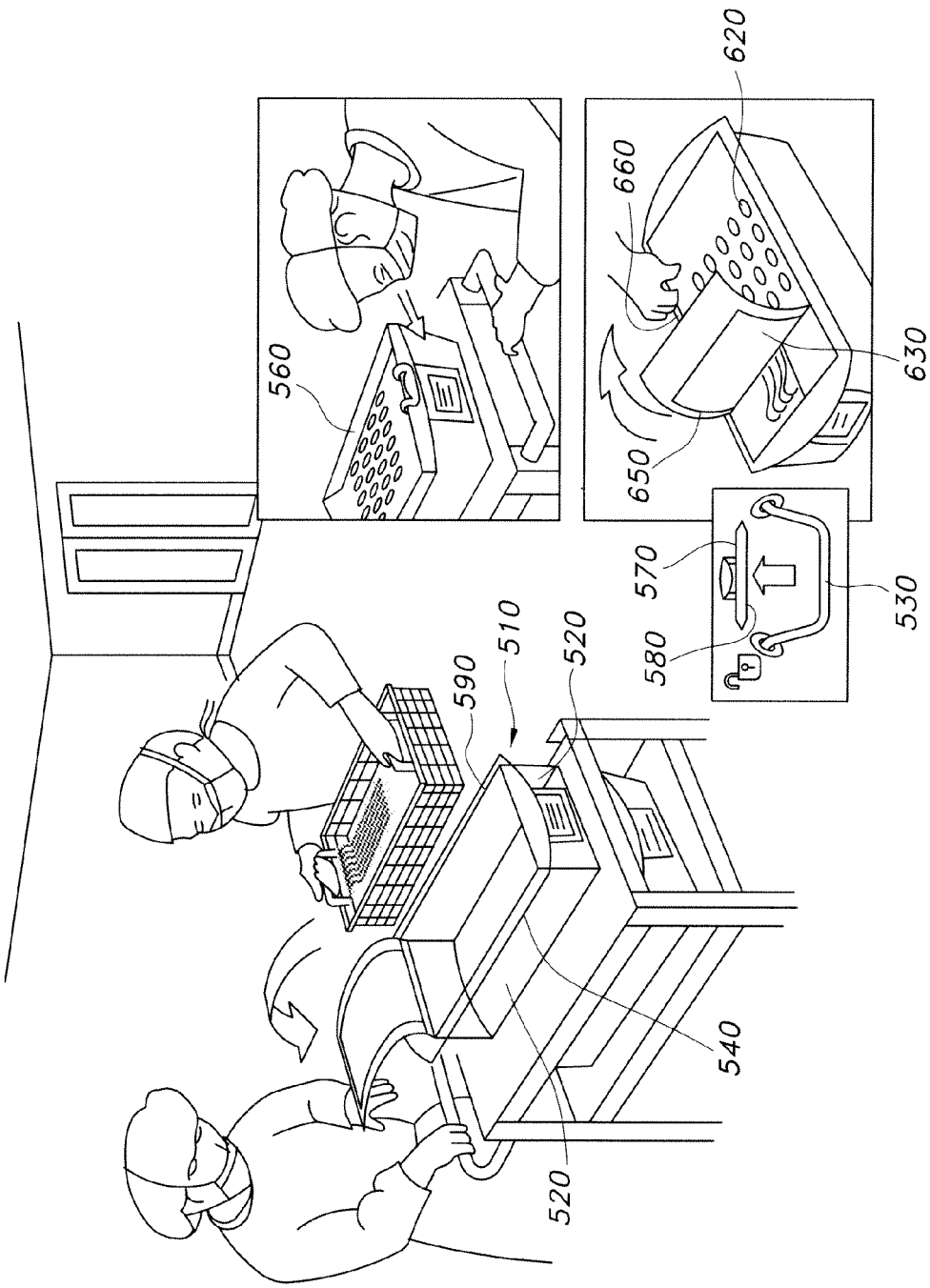
FIG. 29 is a perspective view of an exemplary single use sterilization container which includes a filter in communication with the central portion of the lid.

Turning to FIG. 29, a single use sterilization container is provided. The sterilization container includes a tray 510 and a lid 520. The tray may be made of a rigid material that is substantially transparent. That is, the tray may be made of a material that allows a viewer of the tray to visualize the contents of the tray by utilizing normal human visual acuity without opening the tray. Further, the rigid material of tray should allow the tray to withstand the temperature required for sterilization of the tray without degradation of the tray. That is, the tray (and the lid) should be able to withstand sterilization temperatures of from about 135° F. (59° C.) for some gas or plasma sterilization processes to about 300° F. (149° C.) for certain steam sterilization processes without melting, bending, or losing strength. For example, the materials used for the tray and the lid should be able to withstand steam sterilization temperatures ranging from about 266° F. (130° C.) to about 300° F. (149° C.) without melting, bending, or losing strength. As another example, the materials used for the tray and the lid should be able to withstand steam sterilization temperatures of about 273° F. (134° C.) without melting, bending, or losing strength. Suitable materials for use in the tray include, but are not limited to, various plastics including polyethylenes and polypropylenes.

The tray may be a variety of shapes and sizes including, but not limited to, circular, oblong, trapezoidal, triangular, rectangular, and square. Additionally, the tray includes a base 530 a rim 540 and may comprises a plurality of sides 520.

Regardless of the shape, size, or number of sides, the tray should be adapted to receive a lid 560 in communication with it. Like the tray, the lid may also be composed of a rigid material that may or may not be transparent, such as, for example, various plastics including polypropylene and polyethylene.

Regardless of the type of material that makes up the lid, the lid should include a top side 570, bottom side 580, central portion 600 and peripheral portion 590. In practice, medical instruments for use during a sterilization procedure are placed inside the tray 510. Typical gas sterilization procedures include, for example, gas plasma sterilization, steam sterilization, ethylene oxide sterilization, hydrogen peroxide sterilization, and ozone sterilization.

Once the instruments are placed with the tray, the lid is then snapped onto the tray prior to entering a sterilization chamber. Desirably the lid will include one or more locking mechanisms that allow the peripheral portion of the lid to fixedly engage the rim of the tray. That is, the peripheral portion locks together with the tray and cannot be removed without sufficient force necessary to destroy either a portion of the locking mechanism, the rim, the lid, or combinations thereof so that the tray cannot be easily reconditioned repaired or reused.

Figure 31:
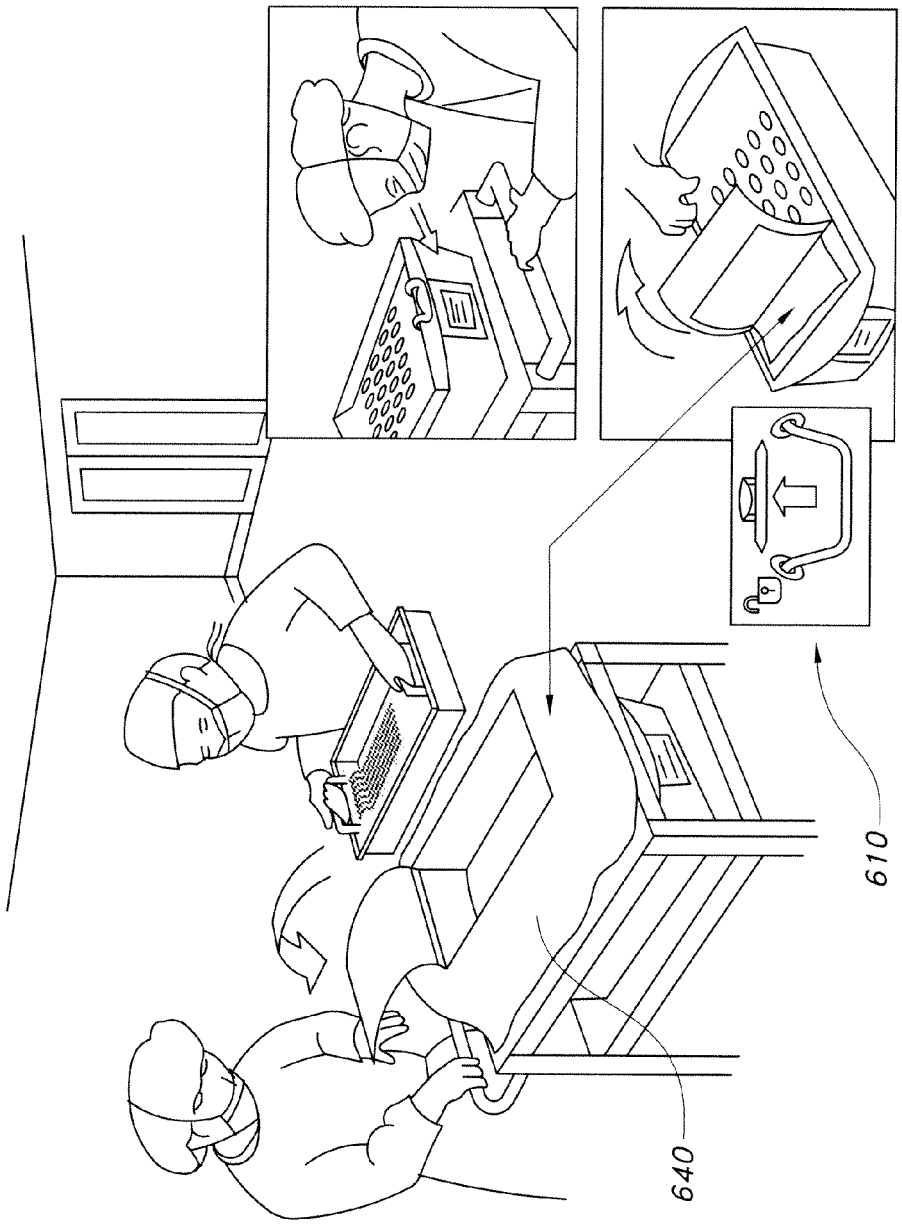
FIG. 31 is a perspective view of an exemplary single use sterilization container which includes a sterilization wrap attached to the peripheral portion of the lid.

Turning to FIG. 31, suitable locking mechanisms include, but are not limited to projections that extend from the peripheral portion of the lid and that fixedly engage the rim of the tray. These projections include, but are not limited to, cantilevered projections 610. Returning to FIG. 29, the central portion of the lid may also include at least one opening 620 therein and filter 630 which is at least in partial communication with the at least one opening, either on the bottom side or top side of the lid. The opening(s) and filter allow the sterilant to pass through the outside of the sterilization container into the inside of the sterilization container where the medical instruments may be contacted with the sterilant during the sterilization process.

Turning to FIG. 31, as an alternative to a filter, a sterilization wrap 640 may be in communication with the bottom side of the lid and attached to the peripheral portion of the lid. Similar to a filter, the sterilization wrap and opening(s) allow the sterilant to pass through the outside of the sterilization container into the inside of the sterilization container where the medical instruments may be contacted with the sterilant during the sterilization process.

Virtually any gas permeable material may be used in conjunction with or as alternative to a filter or sterilization wrap, provided that the material is permeable to a sterilizing gas but impermeable to airborne microbes, bacteria, viruses and mixtures thereof. Suitable gas permeable materials useable in the present invention include, for example, medical grade paper, nonwoven materials and other similar gas permeable materials. Generally, gas permeable materials which may be used in the present invention are permeable to water vapor and have a minimum water vapor transmission rate (WVTR) of about 300 $g/m^2/24$ hours, calculated in accordance with ASTM Standard E96-80. Suitable medical grade paper includes, for example, AMCOR PLP reinforced coated paper available from AMCOR, Limited.

Suitable nonwoven materials useable as the gas permeable material of the sterilization container of the present invention include, for example, air laid nonwoven webs, spunbond nonwoven webs, meltblown nonwoven webs, bonded-carded-webs, hydroentangled nonwoven webs, spunlace webs and the like. The method of manufacturing each of these materials is known in the art. Laminates of these materials may also be used.

Of these nonwoven materials, the fibrous material web may comprise a nonwoven meltblown web. Meltblown fibers are formed by extruding a molten thermoplastic material through a plurality of fine, usually circular, die capillaries as molten fibers into converging high velocity gas (e.g. air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin, et al. Generally speaking, meltblown fibers may be microfibers that may be continuous or discontinuous, and are generally smaller than 10 microns in diameter, and are generally tacky when deposited onto a collecting surface.

The nonwoven material web may be a nonwoven spunbond web. Spunbonded fibers are small diameter substantially continuous fibers that are formed by extruding a molten thermoplastic material from a plurality of fine, usually circular, capillaries of a spinnerette with the diameter of the extruded fibers then being rapidly reduced as by, for example, eductive drawing and/or other well-known spunbonding mechanisms. The production of spun-bonded nonwoven webs is described and illustrated, for example, in U.S. Pat. No. 4,340,563 to Appel, et al., U.S. Pat. No. 3,692,618 to Dorschner, et al., U.S. Pat. No. 3,802,817 to Matsuki et al., U.S. Pat. No. 3,338,992 to Kinney, U.S. Pat. No. 3,341,394 to Kinney, U.S. Pat. No.

3,502,763 to Hartman, U.S. Pat. No. 3,502,538 to Levy, U.S. Pat. No. 3,542,615 to Dobo, et al., and U.S. Pat. No. 5,382,400 to Pike, et al. Spunbond fibers are generally not tacky when they are deposited onto a collecting surface. Spunbond fibers can sometimes have diameters less than about 40 microns, and are often between about 5 to about 20 microns.

The nonwoven material web may also comprise a laminate material such as a spunbond/meltblown/spunbond, or SMS, material. A typical SMS material is described in U.S. Pat. No. 4,041,203 to Brock et al. Other SMS products and processes are described, for example, in U.S. Pat. No. 5,464,688 to Timmons et al.; U.S. Pat. No. 5,169,706 to Collier et al.; and U.S. Pat. No. 4,766,029 to Brock et al. Generally, an SMS material will consist of a meltblown web sandwiched between two exterior spunbond webs. Such SMS laminates are available commercially from Kimberly-Clark Corporation under marks such as Kimguard®. The spunbonded layers on the SMS laminates provide durability and the internal meltblown layer provides porosity.

As discussed above, once the sterilization containers of the present invention containing the items to be sterilized are placed within the sterilization chamber, the sterilization chamber is closed and a gas sterilant is introduced into the container. The amount of time the items in the compartment are subjected to the gas sterilant depends on various factors, including the type of gas sterilant used, the number of medical instruments placed in the sterilization container as well as other factors. Those skilled in the art will be able to determine the appropriate amount of time the gas sterilant should remain in the chamber based on these and other factors.

Figure 30:
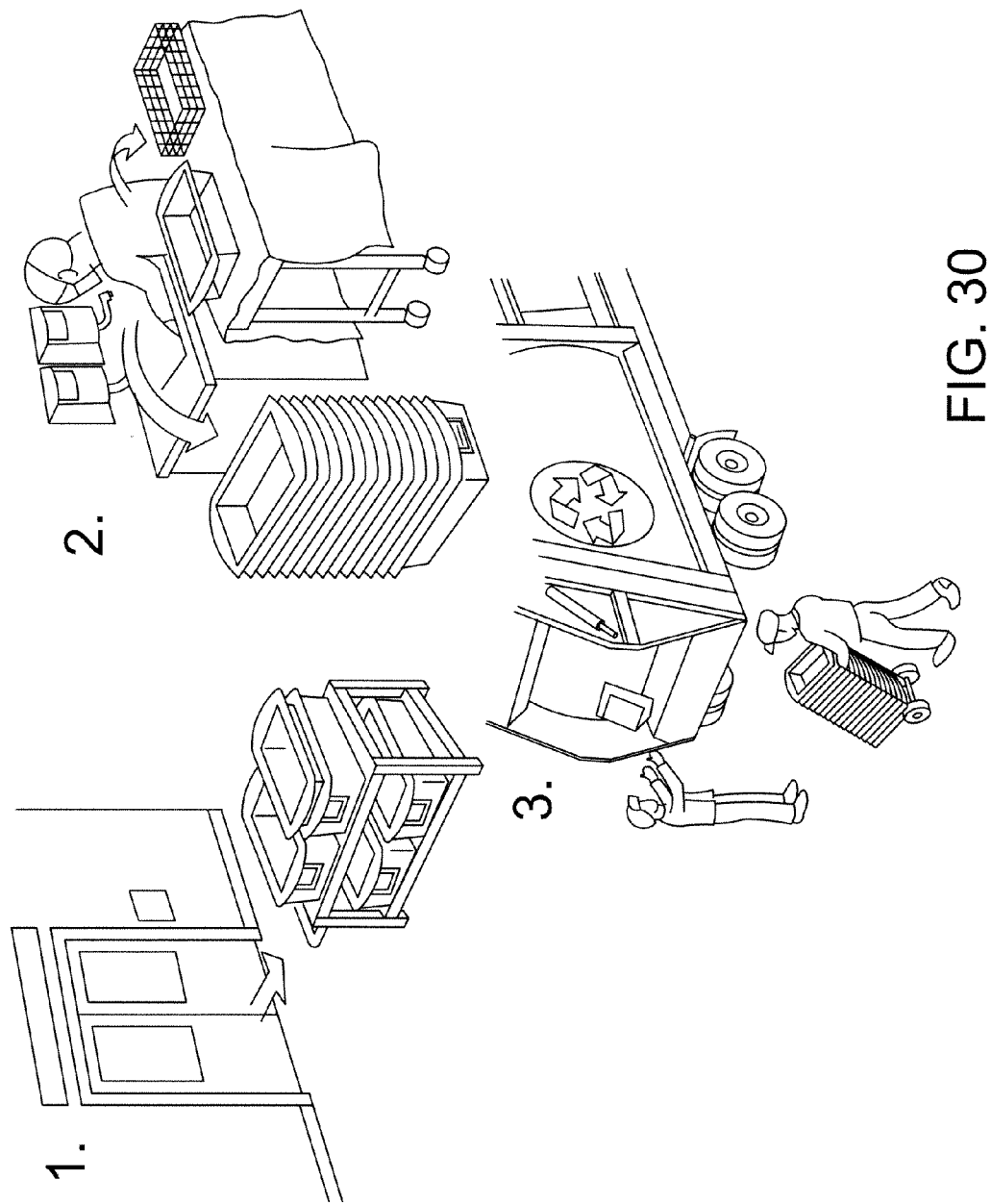
FIG. 30 is an illustration of exemplary single use sterilization containers after use.

Once sterilized, the sterilization containers are removed from the chamber and the sterilization container with the sterilized items contained therein are stored or placed for use. Turning to FIG. 30, after use, the medical instruments are cleaned and the sterilization containers may be stacked and disposed of or recycled.

Returning to FIGS. 29 and 31, advantageously, the central portion of the lid is defined by a frangible region having a plurality of frangible elements 650. These frangible elements may include, but are not limited to scores, perforations, embossments, seams or combinations thereof as known in the art. These frangible elements create a weaker, less sturdy region within the lid of the container which is adapted to tear or rupture upon application of sufficient force. That is, the frangible region should rupture with the use of ordinary force applied to it by a medical or hospital worker.

Additionally, the central portion may include a means for removal 660 of the central portion. The means for removal may be a hook, handle, tab, body parts, or the like. The frangible region may be activated by applying force or pressure to the frangible elements by use of the means for removal. That is, the frangible region should rupture with the use of ordinary force applied to it by a medical or hospital worker, i.e. one hand applying force to the means for removal. Advantageously the force required for removal of the central portion is concentrated near the means for removal. This lowers the force required for removal. After activation of the frangible region, the central portion of the lid is permanently removed. Thus, after sterilization, and upon removal of the central portion from the lid, the central portion cannot be rejoined with the lid to create a closed sterilization container, and the sterilization container cannot be reused. This is a safety feature designed to prevent the accidental use of non-sterile medical instruments.

Of note, although the frangible region should be flexible enough to allow ease of removal of the central portion, it should be sturdy enough for sterilization containers to be stored, stacked, and/or handled without rupturing the frangible region. Additionally, the filter 630 or sterilization wrap 640 should overlap the frangible region so that bacteria or other harmful material does not pass through the frangible elements into the inside of the sterilization container after a sterilization procedure has been completed.

As shown in FIG. 31, in embodiments where a sterilization wrap is utilized the sterilization wrap is folded and attached to the peripheral portion of the lid. Upon removal of the central portion of the lid, the sterilization wrap may be unfolded outward to cover the non-sterile sides and edges of the sterilization container. This allows the clinician to safely and confidently remove the medical instruments from the sterilization container without compromising the sterility of the instruments.

In addition to the sterilization containers described above, the present invention encompasses a method for sterilizing items for use in a medical procedure. This method includes providing a sterilization container having a tray having a plurality of sides, a base and a rim. The tray may be formed of a substantially transparent material adapted to withstand exposure to steam and ethylene oxide sterilization without degradation of the tray. The sterilization container also includes a lid having a top side, a bottom side, a peripheral portion, and a central portion. The peripheral portion of the lid, which is adapted to fixedly engage the rim of the tray, includes a locking mechanism that engages the rim. The central portion of the lid includes at least one opening therein. The central portion is further defined by a frangible region comprising a plurality of frangible elements and includes a means for removal of the central portion by activation of the frangible region. The sterilization container also includes a filter positioned in communication with a side of the lid. The filter is gas permeable and is adapted for removal with the central portion when access to medical instruments is desired. The method also includes placing medical instruments inside the sterilization container; inserting the sterilization container into a sterilization chamber for a length of time sufficient to sterilize the medical instruments; and removing the sterilization container from said sterilization chamber. The method may further include the step of providing instructions regarding accessing the sterilized items by removing the central portion with the means for removal of the central portion by activation of the frangible region.

We claim:

1. A non-reusable, locking container for sterilizing and storing surgical materials and presenting surgical materials in a sterilized condition, the container comprising:
   a tray comprising a base, a plurality of sides each having a proximal portion in communication with the base and a distal portion away from the base, and a rim defined by the distal portions of the sides, the rim comprising a lower portion of a barrier;
   a lid comprising a central portion, and a lip, the lip comprising an upper portion of a barrier, wherein the lid and the tray together define a chamber for containing surgical materials and wherein the lip and the rim together form a barrier to inhibit the passage of microorganisms into the chamber between a tray and lid secured together;
   a permeable filter providing a path for a sterilant to enter the chamber from outside the container and for maintaining aseptic conditions inside the chamber after sterilization;
   a non-reusable lock for securing the tray and the lid together, the non-reusable lock comprising an upper lock element forming a portion of the lid, and a lower lock element forming a portion of the tray, the lower and upper lock elements fixedly engaging into a non-reusable lock when the lid is mated to the tray to seal the container; and a frangible release in communication with the non-reusable lock for irreversibly detaching the non-reusable lock from only one of the tray or the lid such that the non-reusable lock remains joined to the other upon separation of the tray and lid to access the chamber after sterilization, wherein: (a) the lower lock element is incorporated in the rim of the tray, (b) the upper lock element is incorporated in a peripheral portion of the lid that surrounds the central portion of the lid and includes the lip, (c) the frangible release is a frangible region defined in the lid which separates the peripheral portion of the lid from the central portion of the lid, and (d) the central portion of the lid further comprises a means for removal of the central portion by activation of the frangible region, whereby the peripheral portion of the lid and the rim of the tray fixedly engage into a non-reusable lock when the lid is mated to the tray to seal the container and whereby activation of the frangible region irreversibly detaches the central portion of the lid while the non-reusable lock remains joined to the tray.

2. The container of claim 1, wherein the barrier defines a tortuous path from the outside of the container to the chamber to inhibit the passage of microorganisms.

3. The container of claim 1, wherein the barrier provides a seal between the tray and the lid to inhibit the passage of microorganisms.

4. The container of claim 1, wherein the non-reusable lock includes lock elements that mechanically interlock to fixedly engage into a non-reusable lock to secure the lid and the tray together at least at one location.

5. The container of claim 4, wherein the lock elements fixedly engage into a non-reusable lock to secure the lid and the tray together at least at one location further utilizing a material that is heat activated during steam sterilization selected from a shape changeable element, an adhesive, or combinations thereof.

6. The container of claim 1, wherein the non-reusable lock includes lock elements that employ a material that is heat activated during steam sterilization to fixedly engage into a non-reusable lock to secure the lid and the tray together at least at one location.

7. The container of claim 6, wherein the material that is heat activated during steam sterilization is selected from a shape changeable element, an adhesive, or combinations thereof.

8. The container of claim 7, wherein the shape changeable material or adhesive is selected from polyolefins, block copolymers, resins, waxes and combinations thereof.

9. The container of claim 8, wherein the shape changeable material or adhesive has a melting point of less than 134 degrees Centigrade.

10. The container of claim 1, wherein the frangible release is activated by travel or movement of the non-reusable lock away from the tray or lid.

11. The container of claim 1, wherein the filter is in the central portion of the lid.

12. The container of claim 1, wherein the frangible region comprises a plurality of frangible elements selected from scores, perforations, embossments, seams or combinations thereof.

13. The container of claim 1, wherein the means for removal of the central portion is a hook, handle or a tab.

14. The container of claim 1, further comprising sterilization wrap attached to the peripheral portion of the lid and positioned in communication with a bottom side of the lid so that the sterilization wrap remains attached to the peripheral portion of the lid during irreversible detachment of the central portion of the lid and is presented for unfolding after the central portion of the lid is removed.

15. A non-reusable, locking container for sterilizing and storing surgical materials and presenting surgical materials in a sterilized condition, the container comprising:

a tray comprising a base, a plurality of sides each having a proximal portion in communication with the base and a distal portion away from the base, and a rim defined by the distal portions of the sides, the rim comprising a lower portion of a barrier;

a lid comprising a central portion, and a lip, the lip comprising an upper portion of a barrier, wherein the lid and the tray together define a chamber for containing surgical materials and wherein the lip and the rim together form a barrier to inhibit the passage of microorganisms into the chamber between a tray and lid secured together;

a permeable filter providing a path for a sterilant to enter the chamber from outside the container and for maintaining aseptic conditions inside the chamber after sterilization;

a non-reusable lock for securing the tray and the lid together, the non-reusable lock comprising an upper lock element forming a portion of the lid, and a lower lock element forming a portion of the tray, the lower and upper lock elements fixedly engaging into a non-reusable lock when the lid is mated to the tray to seal the container; and a frangible release in communication with the non-reusable lock for irreversibly detaching the non-reusable lock from only one of the tray or the lid such that the non-reusable lock remains joined to the other upon separation of the tray and lid to access the chamber after sterilization, wherein: (a) the lower lock element is incorporated in the distal portions of the sides of the tray and includes the rim of the tray, (b) the upper lock element is incorporated in a peripheral portion of the lid that surrounds the central portion of the lid and includes the lip, (c) the frangible release is a frangible region defined in the distal portions of the sides of the tray and which separates the rim of the tray from proximal portions of the sides of the tray, and (d) the distal portions of the sides of the tray further comprises a means for removal of the lid and the rim of the tray by activation of the frangible region, whereby the rim of the tray and the peripheral portion of the lid fixedly engage into a non-reusable lock when the lid is mated to the tray to seal the container and whereby activation of the frangible region irreversibly detaches the rim from the tray while the non-reusable lock remains joined to the lid.

* * * * *